US006399385B1

(12) United States Patent
Croyle et al.

(10) Patent No.: US 6,399,385 B1
(45) Date of Patent: Jun. 4, 2002

(54) METHODS FOR RAPID PEG-MODIFICATION OF VIRAL VECTORS, COMPOSITIONS FOR ENHANCED GENE TRANSDUCTION, COMPOSITIONS WITH ENHANCED PHYSICAL STABILITY, AND USES THEREFOR

(75) Inventors: Maria Croyle, Austin, TX (US); James M. Wilson, Gladwyne, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/670,277

(22) Filed: Sep. 27, 2000

Related U.S. Application Data

(60) Provisional application No. 60/156,808, filed on Sep. 2, 1999.

(51) Int. Cl.[7] .................... C12N 15/861; C12N 15/864; C12N 15/63; C12N 7/01
(52) U.S. Cl. .................... 435/456; 435/320.1; 435/455; 435/457; 435/235.1; 435/243; 435/247; 435/250; 435/260; 424/93.2; 424/93.1; 424/93.6
(58) Field of Search .............................. 435/320.1, 455, 435/456, 457, 235.1, 243, 247, 250, 260; 424/93.2, 93.1, 93.6

(56) References Cited

FOREIGN PATENT DOCUMENTS

| WO | WO 98/39465 | 9/1998 |
|---|---|---|
| WO | WO 98/39467 | 9/1998 |
| WO | WO 98/44143 | 10/1998 |
| WO | WO 00/29024 | 5/2000 |
| WO | WO-95/106-01 | * 4/2001 |

OTHER PUBLICATIONS

Maria A. Croyle et al, Development of a Rapid Method for the PEGylation of Adenoviruses with Enhanced Transduction and Improved Stability under Harsh Storage Conditions, Human Gene Therapy 11:1713–1722, Aug. 10, 2000.*
Francis et al., "PEGylation of Cytokines and Other Therapeutic Proteins and Peptides:the Importance of Biological Optimisation of Coupling Techniques". *International Journal of Hematology*, 68:1–18 (Jul. 1998).
Kita et al., "Characterization of a Polyethylene Glycol Conjugate of Recombinant Human Interferon", *Drug Design and Delivery*, 6:157–167 (Sep. 1990).
Peracchia et al., "Pegylated Nanoparticle from a Novel Methoxypolyethylene Glycol Cyanoacrylate–Hexadecyl Cyanoacrylate Amiphiphilic Copolymer", *Pharmaceutical Research*, 15(4):550 (Apr. 1998).

Delgado et al., "The Uses and Properties of PEG–Linked Proteins", *Critical Review in Therapeutic Drug Carrier Systems*, 9(3,4):249–304 (1992).
Francis et al., "Polyethylene Glycol Modification: Relevance of Improved Methodology to Tumour Targeting", 3:321–340 (1996).
Richter et al., "Antibodies Against Polyethylene Glycol Produced in Animals by Immunization with Monomethoxy Polyethylene Glycol Modified Proteins", *Int. Archs Allergy Appl. Immun.*, 70:124–131 (1983).
O'Riordan et al., "PEGylation of Adenorvirus with Retention of Infectivity and Protection from Neutralizing Antibody in Vitro and in Vivo", *Human Gene Therapy*, 10:1349–1359 (May 20, 1999).
Croyle et al., "Stealth Viruses as Efficient Vectors for Gene Therapy", *1999 AAPS Annual Meeting Abstracts Online*, vol. 1, issue 4, Abstract#4110, published Sep. 29, 1999.
M. A. Croyle et al., "Development of Novel Formulations That Enhance Adenoviral–Mediated Gene Expression in the Lung *in Vitro* and *in Vivo*", *Molecular Therapy*, vol. 4, No. 1, pp. 22–28 (Jul. 2001).
D. Fisher et al., "Factors with Impact on the Success of Protein and Virus Pegylation", *Polymer Preprints*, 41(1), pp. 1012–1013 (Mar. 2000).
M. A. Croyle et al., "Beta Cyclodextrins Enhance Adenoviral–Mediated Gene Delivery to the Intestine", *Pharmaceutical Research*, vol. 15, No. 9, pp. 1348–1355 (1998).
T. Ohsawa et al., "Enhancement of Adenovirus–Medicated Gene Transfer into Dermal Fibroblasts *In vitro* and *In vivo* by Polyethylene Glycol 6000", *Journal of Dermatology*, 27: 244–251 (Apr. 2000).
M. A. Croyle et al., "Development of a Rapid Method for the PEGylation of Adenoviruses with Enhanced Transaction and Improved Stability under Harsh Storage Conditions", *Human Gene Therapy*, 11: 1713–1722 (Aug. 10, 2000).
M. A. Croyle et al., "Stealth Adenoviruses Blunt Cell–Meditated and Humoral Immune Responses against the Virus and Allow for Significant Gene Expression upon Readministration in the Lung", *Journal of Virology*, vol. 75, No. 10, pp. 4792–4801 (May 2001).

* cited by examiner

*Primary Examiner*—David Guzo
(74) *Attorney, Agent, or Firm*—Howson and Howson

(57) ABSTRACT

A rapid method for modifying a viral capsid or envelope protein with a polyethylene glycol (PEG) is described. Also provided are methods of delivering a molecule using the PEG-modified viruses of the invention. Compositions containing the PEG-modified viruses of the invention, are characterized by improved gene expression, reduced neutralizing antibody and CTL production. Also provided are viral compositions having enhanced physical stability, in which the viruses are lyophilized in a formulation having a 1:1 ratio of sucrose and mannitol are provided.

34 Claims, 2 Drawing Sheets

METHODS FOR RAPID PEG-MODIFICATION OF VIRAL VECTORS, COMPOSITIONS FOR ENHANCED GENE TRANSDUCTION, COMPOSITIONS WITH ENHANCED PHYSICAL STABILITY, AND USES THEREFOR

CROSS-REFERENCE TO RELATED APPLICATION

This application claims the benefit of U.S. patent application Ser. No. 60/156,808, filed Sep. 29, 1999.

This work was funded by in part by grants from the NIH [P30 DK47757-05,-07 and PO1 HL59407-02] and NIH/NIAMS [P01 AR/NS43648-04]. The US government may have certain rights in this invention.

FIELD OF THE INVENTION

The invention relates generally to the field of gene delivery into host cells, and more particularly, to gene delivery via viral vectors.

BACKGROUND OF THE INVENTION

Viral-mediated gene delivery has been described for delivery of therapeutic genes to patients. One limitation of currently known methods is the generation of neutralizing antibodies (NAB) by the patients immune response against viral capsids, which prohibit significant levels of gene expression upon readministration. Thus, methods of gene delivery which circumvent these immune responses are needed.

Covalent modification of proteins and enzymes with functionalized poly(ethylene) glycol (PEG) has been studied. PEG is an uncharged, hydrophilic, linear polymer that is non-immunogenic and has a very low order of toxicity. Recently, O'Riordan et al have developed a process to covalently link various polyethylene glycols to the capsid proteins of adenovirus [O'Riordan et al, *Hu Gene Therapy*, 10: 1349–1358 (1999)]. However, this method requires incubation for a period of 20 to 24 hours.

What is needed are viral vectors which avoid the limitations of current constructs for re-administration, as well as rapid methods for generating high levels of such constructs.

SUMMARY OF THE INVENTION

In one aspect, the invention provides a method for conjugating a recombinant virus with polyethylene glycol to enhance transduction efficiency thereof. This method involves the steps of reacting activated PEG and a recombinant virus at room temperature for about 15 minutes to about 2 hours; and stopping the reaction, thereby obtaining PEG-conjugated virus. Most suitably, the activated PEG and the recombinant virus are reacted at a ratio of about 10:1 polyethylene glycol to virus. Desirably, the recombinant virus is present at a concentration of about $1 \times 10^{10}$ to about $1 \times 10^{15}$ particles per ml of reaction solution.

In another aspect, the invention provides a PEG-conjugated virus prepared according to the method of the invention.

In yet another aspect, the invention provides a method for increasing transduction efficiency of a recombinant virus which involves delivering a modified recombinant virus according to the invention to host cells.

In still another aspect, the invention provides a method for re-administration of a molecule to a selected host cell via a viral vector. This method involves the steps of contacting the host cell with a PEG-modified virus according to the invention, wherein said virus comprises a molecule for delivery to a host cell; and contacting the host cells with a recombinant virus comprising the molecule.

In yet a further aspect, the invention provides a composition useful for delivery of a selected molecule to host cells. The composition contains a PEG-conjugated virus prepared according to the method of the invention and a physiologically acceptable carrier.

In still a further aspect, the invention provides a composition that enhances the physical stability of viral vectors. This composition contains a recombinant viral vector comprising a molecule for delivery to host cells, sucrose, and mannitol, wherein the ratio of sucrose to mannitol is about 1 to about 1. Desirably, the composition is lyophilized to a final moisture content of about 1.2% to about 1.7%.

Other aspects and advantages of the invention will be apparent from the following detailed description of the invention.

DETAILED DESCRIPTION OF THE INVENTION

Figure 1A:
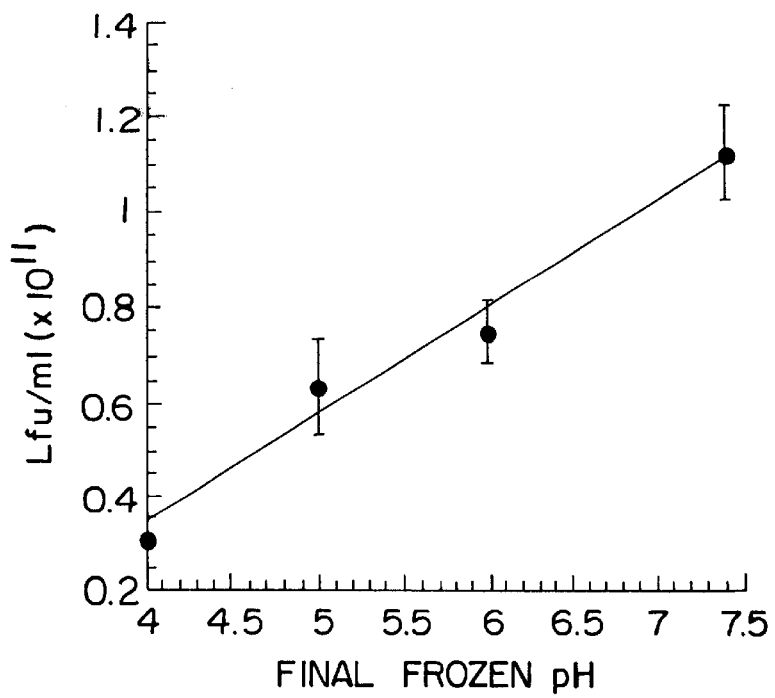
FIG. 1A illustrates the results of a study on the effect of the final frozen pH of a formulation on adenovirus stability (correlation coefficient, $r^2=0.98$). See Example 15. The results are reported as the average titer of 4–6 samples from two separate experiments. Error bars reflect the standard deviation of the data.

The invention provides a novel, rapid, method of modifying a protein or enzyme with an activated polyethylene glycol (PEG) polymer. Advantageously, the modification method described herein is complete within a short period of time (e.g., about 1 to 2 hours), occurs under mild conditions (e.g., room temperature, physiologic pH), and enhances physical stability under extreme storage conditions.

This method has been found to be particularly well suited for modification of the capsid protein of viral vectors. Advantageously, substantial gene expression has been obtained using the PEG-modified viral vectors of the invention upon re-administration intravenously and intramuscularly without compromising the recipient's immune system against other pathogens. The vectors of the invention are also useful for delivery by other routes. The modified vectors of the invention are particularly useful in therapies that require chronic treatment. Further, these modified vectors allow for significant levels of gene expression in patients with high titers of neutralizing antibodies. In addition, re-administration can occur with the native virus after prior exposure to the modified virus.

Thus, the PEG-modification method of the invention is particularly well suited for modification of recombinant viruses which contain a desired molecule for delivery to a host cell within a capsid or envelope protein. In one particularly desirable embodiment, the molecule for delivery is a nucleic acid sequence encoding a transgene under the control of regulatory sequences which direct its expression in the host cell. In another desirable embodiment, the molecule for delivery is a protein, chemical, enzyme, or other moiety. Selection of the molecule for delivery is not a limitation of the present invention.

In a particularly desirable embodiment, the methods of the invention are used in connection with adeno-associated viruses. However, these methods may be readily applied to other viruses which contain their genetic material within capsid or envelope proteins. Examples of other suitable viruses having capsids or envelopes suitable for PEG-modification include, adenoviruses, retroviruses, lentiviruses, among others. For convenience throughout the specification, reference will be made to capsid proteins. However, it will be understood that similar methods may be applied to modify viral envelope proteins. Similarly, the methods of the invention may be readily used to modify other proteins and enzymes, whether viral or non-viral. As defined herein, polyethylene glycol (PEG) is a polymer composed of repeating units of the formula: H—(OCH$_2$CH$_2$)$_n$—OH, where n is 2 to about 1000. Most suitably, the invention uses a PEG compound having a molecular weight in the range selected from about 500 to about 500,000, about 1000 to about 200,000, and about 5000 to 100,000. Encompassed within this definition are substituted PEG compounds. In a currently preferred embodiment, the substituted PEG is monomethyoxypolyethylene glycol (MPEG) having a molecular weight of 5000. MPEG has the formula CH$_3$—(OCH$_2$CH$_2$)$_n$—OH and may be generated by conventional synthesis techniques or purchased commercially. Other suitable substituted PEG compounds can be readily determined, or designed, particularly to present a chemical group suited to activation and/or as a point of attachment to the viral protein capsid.

MPEG (or another selected PEG) is chemically activated prior to coupling to the selected protein (e.g. virus capsid) or enzyme. The chemical activation may be performed using conventional techniques. Activated MPEG may be purchased from a variety of commercial sources. For example, tresyl-MPEG (TMPEG), succinimidyl succinate-MPEG (SSMPEG), and cyanuric chloride-MPEG (CCMPEG) may be obtained from Sigma Chemicals (St. Louis, Mo.). Alternatively, MPEG may be activated with succinimidyl activate esters according to the following scheme:

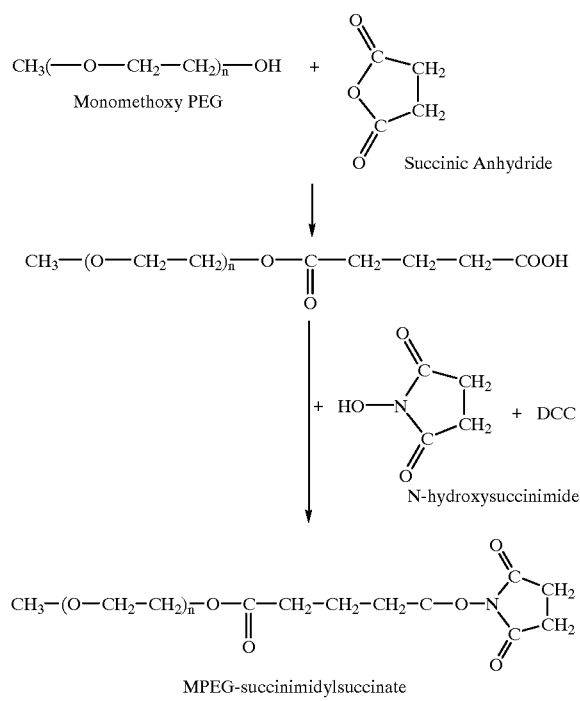

MPEG may be activated with tresyl chloride according to the following scheme:

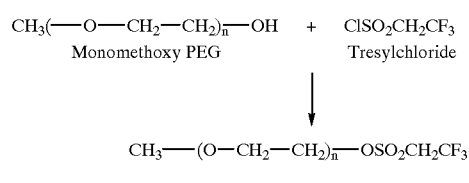

MPEG may be activated with cyanuric chloride according to one of the following two schemes:

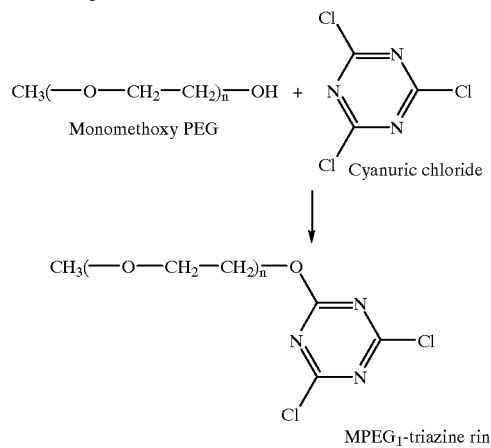

Another suitable scheme for activation of MPEG with cyanuric chloride is as follows:

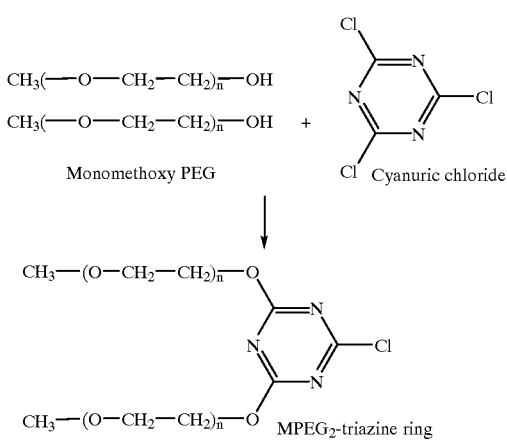

Regardless of the activation compound or method utilized, the activated MPEG is thereafter conjugated with the selected protein (e.g., viral capsid) using the method of the invention, which is more rapid and performed under less stringent conditions, as compared to the prior art methods [see, e.g., Delgaldo, *Biotechnol. Appl. Biochem.*, 12:119–128 (1999)]. More particularly, the methods in the art required incubation for a period of 20 to 24 hours, and in some cases involved the step-wise addition of varying concentrations of activated PEG at regular intervals during the incubation period. The resulting product was a "super-pegylated virion". Advantageously the method of the invention eliminates this requirement for addition of activated PEG at regular intervals, and provides a PEG-modified product in about 1 to 2 hours.

According to the method of the invention, the protein selected for modification (e.g., the viral capsid) is preferably purified from any contaminants. For example, a viral vector may be produced using methods known to those of skill in the art [See, e.g., K. J. Fisher et al, *J. Virol*, 70:520–532 (1996)]. Thereafter, the viral vector is preferably purified by conventional methods. For example, cesium chloride (CsCl) gradients [K. J. Fisher et al, *Nat. Med.*, 3:306–312 (1997)] and column chromatography methods are particularly desirable. A variety of columns useful for purification are available commercially (e.g., Bio-Rad, Perseptive Biosystems, etc.) and other methods have been described in the literature. Selection of the method of purification is not a limitation of the present invention.

Suitably, the construct (e.g., purified viral vector) selected for PEG-modification is desalted to remove any residual salt from the purification process (e.g., CsCl) or storage medium. In one desirable embodiment, this desalting is performed on a commercially available chromatography column. Following desalting, the viral vector is equilibrated with a buffer compatible with the PEG-conjugation reaction described below, or a formulation that enhanced viral stability upon long-term storage. Suitably, the vector may be equilibrated with the buffer selected for use in the conjugation reaction. The buffer may be selected taking into consideration such factors as convenience and the type of activated PEG used in the reaction.

For example, when the construct is to be conjugated with TMPEG according to the invention, a particularly desirable buffer is potassium phosphate buffer (KPBS) at a pH of about 7 to about 8, and most preferably 7.4. For conjugation with SSMPEG and CCMPEG, purified protein (e.g., bands from the CsCl gradients) are desalted in sodium phosphate (pH about 6.5 to about 7.5, and most preferably 7.2) and sodium tetraborate (pH about 8.5 to about 9.9, and most preferably 9.2) buffers. However, given these parameters, one of skill in the art may adjust these buffers as needed.

Once the protein is desalted (if necessary) and equilibrated with the selected buffer, the selected activated PEG is combined with the virus to form a reaction mixture of PEG and protein, in which the activated PEG is present in a PEG-to-virus ratio in the range of 1:1 to 20:1, and about 5:1 to 15:1. Where the virus is rAAV, a ratio of 10:1 is preferred. However, one of skill in the art can readily adjust these ratios, as desired. Suitably, the reaction mixture is performed at room temperature (e.g., about 22° C. to 24° C.) under gentle stirring for about 15 minutes to about 120 minutes and the reaction is stopped. One desirable method of stopping the reaction is by adding an excess of L-lysine with respect to the amount of PEG. About a 10-fold excess has been found desirable; however, one of skill in the art could readily select another suitable amount. Alternatively, the reaction may be stopped by lowering the temperature of the reaction to about 40° C. Desirably, the reaction is allowed to proceed until complete (i.e., about 100%) modification of the target protein (e.g., viral capsid) is achieved. However, under certain circumstances, the reaction may be stopped when the modification is less than complete. For example, when certain activated CCPEGs are utilized, it may be desirable to stop the reaction when modification is about 70% complete, in order to avoid agglomeration which is observed with certain types of activated CCPEGs in certain proteins. However, as the advantages of the invention, which include increased transduction efficiency, have been observed with less than 100% modification, it may be desirable to stop the reaction at 70% to 98%, 75% to 95%, 80% to 90%, or 85% completion for a variety of reasons which will be readily apparent to one of skill in the art. The degree of modification can be determined using conventional methods. See, e.g., the fluorescamine assay described in Example 3 herein.

The resulting PEG-modified protein is separated from unreacted PEG, excess lysine and reaction byproducts. Examples of suitable separation methods include CsCl centrifugation or passage of the reaction mixture through a column equilibrated with a suitable buffer (e.g., 10 mM potassium buffered saline (KPBS) at pH 7.4). However, other separation methods may be readily selected. Fractions that contain the PEG-modified construct may thereafter be confirmed by UV spectrophotometric analysis at 260 nm or other suitable methods. After separation (purification) the PEG-modified construct (e.g., virus) may be suspended in a solution suitable for storage and/or delivery to host cells.

Advantageously, the inventors have found that viruses modified by this method retain infectivity. Most suitably, the PEG-modified viruses of the invention avoid incorporation of the activating group into the modified virus, thus avoiding any problems associated with potential immunogenicity of the coupling moiety. Thus, the present invention further provides compositions containing PEG-modified viruses of the invention and a carrier suitable for delivery of the composition to host cells for a variety of therapeutic and other purposes.

COMPOSITIONS OF THE INVENTION

A. PEG-modified Constructs

In one embodiment, a composition of the invention contains a PEG-modified protein or enzyme of the invention and a physiologically compatible carrier. In a particularly desirable embodiment, the invention provides a composition containing a PEG-modified virus. Suitably such a virus encodes a transgene which is under the control of regulatory sequences which direct its expression in a host cell. Alternatively, the virus may carry another molecule for which delivery to the host cell is desirable.

Suitable doses of PEG-modified viruses may be readily determined by one of skill in the art, depending upon the condition being treated, the health, age and weight of the veterinary or human patient, and other related factors. However, generally, a suitable dose may be in the range of $10^{10}$ to $10^{18}$, and preferably about $10^{14}$ to $10^{16}$ viral particles per dose, for an adult human having weight of about 80 kg. This dose may be suspended in about 0.01 mL to about 1 mL of a physiologically compatible carrier and delivered by any suitable means. The dose may be repeated, as needed or desired, daily, weekly, monthly, or at other selected intervals using any suitable delivery means.

Suitably, such a carrier is physiologically compatible, e.g. saline, distilled water, phosphate buffered saline (PBS), potassium (K) PBS, sodium PBS, and the like, suitable for administration to a human or non-human mammalian patient. Other exemplary carriers include sterile saline, lactose, sucrose, calcium phosphate, gelatin, dextran, agar, pectin, peanut oil, sesame oil, and water. The selection of the carrier is not a limitation of the present invention.

Optionally, the compositions of the invention may contain, in addition to the PEG-modified virus and carrier(s), other conventional pharmaceutical ingredients, such as preservatives, chemical stabilizers, or surfactants, may be included in the formulation. Suitable exemplary preservatives include chlorobutanol, potassium sorbate, sorbic acid, sulfur dioxide, propyl gallate, the parabens, ethyl vanillin, glycerin, phenol, and parachlorophenol. For example, suitable chemical stabilizers may include gelatin and albumin. Optionally, a composition of the invention may contain free amino acids, e.g. adenosine, other components such as carbohydrates, surfactants and other stabilizers.

B. Formulations which Enhance Physical Stability

In another aspect, the present invention provides novel formulations which enhances the physical stability of viral vectors even under harsh storage conditions. In one embodiment, these viral vectors are modified according to the method of the present invention. However, the formulations described herein are useful for a variety of other viral vectors, which may be readily selected by one of skill in the art. In addition, the formulations described herein may be desirable for a variety of non-viral vectors, e.g., plasmids, or other DNA or proteins which will be subject to lyophilization, long-term storage under freezer or refrigeration conditions, and shipping.

Suitably, for long-term storage, the viral vector is lyophilized to contain a final moisture content in the range of about 1.2% to 1.7%, and more preferably about 1.3% to 1.4%, in a formulation Desirably, the formulations of the invention contain at least about $5\times10^{10}$ to about $1\times10^{16}$, or about $5\times10^{11}$ viral particles/ml. Where non-viral constructs are utilized, one of skill in the art can readily determine the appropriate concentration of the selected construct. For example, a formulation of the invention may contain about 0.1 µg to about 10 mg DNA, more preferably about 10 µg to about 1 mg DNA, or about 0.1 µg to about 10 mg protein, more preferably about 10 µg to about 1 mg protein. However, other suitable concentrations may be readily selected by one of skill in the art. Using these parameters, lyophilization may be performed using conventional techniques. See, generally, Sambrook et al, Molecular Cloning: A Laboratory Manual, Cold Spring Harbor Laboratories, Cold Spring Harbor, N.Y.

In one particularly desirable embodiment, the construct to be formulated into a composition of the invention (e.g., a viral vector) is combined in solution with sucrose and mannitol. For viral vectors, a ratio of about 1:1 sucrose to mannitol is particularly desirable. However, the ratio of sucrose to mannitol may be adjusted, and more desirably about 3:4 sucrose to mannitol, taking into consideration the stability of the selected construct on storage. For example, in general, an adeno-associated viral vector tends to exhibit better stability than an adenoviral vector under long-term storage conditions. For example, ratios may range from about 4:1 sucrose to mannitol to about 1:4 sucrose to mannitol, and more desirably about 3:4 sucrose to mannitol, and most desirably, about 1:1.

Most preferably, a composition of the invention having enhanced storage stability also contains about 0.5% to 5% beta cyclodextrin (BCD), and most preferably a tertiary amine BCD. In one particularly desirable embodiment, this composition further contains about 0.5 mg/ml to about 1 mg/ml pluronic protamine.

Optionally, the compositions of the invention may contain conventional pharmaceutical ingredients, such as preservatives, carbohydrates, stabilizers, or surfactants, such as those described above.

The compositions of the invention, including the PEG-modified constructs of the invention whether formulated as described above and/or the compositions formulated for long-term storage whether prepared with the PEG-modified constructs or other constructs, may be delivered using methods known to those of skill in the art. Where the PEG-modified vectors (or other constructs) have been lyophilized, the vectors can be readily reconstituted using methods known to those of skill in the art. See, e.g., L. Rey and J. C. May, "Freeze-drying/lyophilizatoin of pharmaceutical and biological products", *Drugs and the Pharmaceutical Sciences*, Vol. 96, 1999, Marcel Dekker: New York, N.Y.; M. J. Pikal, "Freeze-drying of Proteins", Part 1: Process Design., *Biopharm*, 1990, September: p. 18–27; M. J. Pikal, *Biopharm.*, 3(8):28–31 (1990).

METHODS OF THE INVENTION

The invention provides a method of delivering a transgene or other molecule to a human or veterinary patient by delivering a PEG-modified construct to the patient. The target cells may be transduced in vivo or ex vivo, taking into consideration such factors as the selection of target cells and the condition for which the patient is being treated. For convenience, the following discussion will refer to delivery of transgenes by PEG-modified viral vectors. However, these methods may also be used to deliver other PEG-modified constructions and the other compositions of the invention.

A. In vivo

For in vivo delivery of the transgenes, any suitable route of administration may be used, including, direct delivery to the target organ, tissue or site, intranasal, intravenous, intramuscular, subcutaneous, intradermal, vaginal, rectal, and oral administration. Routes of administration may be combined within the course of repeated therapy or immunization.

Suitable doses of PEG-modified viruses may be readily determined by one of skill in the art, depending upon the condition being treated, the health, age and weight of the veterinary or human patient, and other related factors. However, generally, a suitable dose may be in the range of $10^3$ to $10^{18}$, preferably about $10^5$ to $10^{16}$ particles per dose, for an adult having a weight of about 80 kg. This dose may be formulated in a pharmaceutical composition, as described above (e.g., suspended in about 0.01 mL to about 1 mL of a physiologically compatible carrier) and delivered by any suitable means. The dose may be repeated, as needed or desired, daily, weekly, monthly, or at other selected intervals.

B. Ex Vivo

In another embodiment, the PEG-modified viruses of the invention are useful for ex vivo transduction of target cells. Generally, ex vivo therapy involves removal of a population of cells containing the target cells, transduction of the cells in vitro, and then reinfusion of the transduced cells into the human or veterinary patient. Such ex vivo transduction is particularly desirable when the target cells are dendritic cells or macrophages and/or when the transgene or other molecule being delivered is highly toxic, e.g., in the case of some genes used in the treatment of cancer. However, one of skill in the art can readily select ex vivo therapy according to the invention, taking into consideration such factors as the type of target cells to be delivered, the molecule to be delivered, the condition being treated, the condition of the patient, and the like.

Generally, when used for ex vivo therapy, the targeted host cells are infected with $10^5$ viral particles to $10^{10}$ viral particles for each $10^1$ to $10^{10}$ cells in a population of target cells. However, other suitable ex vivo dosing levels may be readily selected by one of skill in the art.

C. Re-Administration

In one embodiment, the invention provides methods of delivering transgenes via PEG-modified viral vectors, in which re-administration or repeat delivery is performed using a PEG-modified vector of the invention in which the activating group of the MPEG differs from the activating group utilized on the PEG-modified vector of the first administration. Thus, the invention may involve delivering a PEG-modified viral vector conjugated with first activated MPEG (e.g., tresyl-MPEG) and a second delivery with the PEG-modified viral vector in which the MPEG is conjugated with a second activated MPEG group (e.g., succinimidyl succinate MPEG, SSPEG). Alternatively, a PEG-modified viral vector of the invention may be used in a dosage regimen in which non-pegylated viral vectors are utilized. Thus, a PEG-modified viral vector of the invention may be delivered prior to delivery of a non-pegylated viral vector. In another example, a delivery of a PEG-modified viral vector of the invention may follow a prior administration with a non-pegylated viral vector.

The following examples are provided to illustrate the methods of preparing the compositions of the invention and the methods of the invention, These examples do not limit the scope of the invention. One skilled in the art will appreciate that although specific reagents and conditions are outlined in the following examples, modifications can be made which are meant to be encompassed by the spirit and scope of the invention.

EXAMPLE 1

Production of Conjugated Adeno-Associated Virus (AAV) Vectors

A. Preparation of Recombinant AAV (rAAV)

rAAV containing LacZ were prepared according to published methods. An rAAV used in the following studies, AAVCMVLacZ, contains AAV 5' and 3' ITRs flanking an *E. coli* β-galactosidase reporter gene expressed under the control of a human cytomegalovirus (CMV) promoter. Another rAAV used in these studies is AAVAlbα1AT, which contains AAV 5' and 3' ITRs flanking a human α1-anti-trypsin (α1AT) gene expressed under the control of the albumin promoter. These were produced using the B50 cell line as described [G.-P. Gao et al, *Hum. Gene Ther.*, 2:2353–2362 (1998)].

B50 cells (a HeLa based cell line expressing AAV Rep/Cap proteins) were infected with wild-type Ad5 at a multiplicity of infection of 10 for 24 hours and then with an Ad-AAV hybrid vector [K. J. Fisher et al, *J. Virol*, 70:520–532 (1996)] at the same multiplicity of infection (MOI) for an additional 48 hours. At this time, cells were harvested, resuspended in 10 mM Tris buffer pH 8.1 and lysed by three freeze/thaw cycles in dry ice/ethanol and 37° C. baths. Benzonase (Nucomed Pharma, pure grade) was added to the mixture (50 U/ml, final concentration) and the lysate incubated at 37° C. for 30 minutes. Lysate was clarified by centrifugation at 3700 g for 20 minutes and supernatant collected. According to established methods [S. Zolotukin et al, *Gene Ther.*, 6:973–985 (1999)], lysate was loaded on a POROS HE 20 (Perseptive Biosystems) column equilibrated with 20 mM PBS (pH 7.5), 250 mM NaCl. After the lysate entered the resin, the column was washed with 10 column volumes of the equilibration buffer. Vector was eluted from the column directly onto a POROS 50 PI column with 20 mM PBS (pH 5.5) 400 mM NaCl. Fractions from the second column were collected, concentrated, and incubated at 56° C. for 10 minutes to inactivate any residual adenovirus in the preparation.

B. Conjugation of Viral Vectors

A monomethoxy derivative of polyethylene glycol (approx. MW 5000) was chosen for conjugation to the rAAV particles. This compound must first be chemically activated prior to the conjugation reaction. Three types of activated monomethoxypolyethyleneglycol (MPEG) were used in this study: tresyl-MPEG (TMPEG), succinimidyl succinate MPEG (SS-PEG), and cyanuric chloride MPEG (CC-MPEG). All activated PEGs were obtained from Sigma Chemicals (St. Louis, Mo.). In all cases, conjugation reactions were performed using a modification of established methods [Delgado, *Biotechnol. Appl. Biochem.*, 12:119–128 (1990); Kita, *Drug Design & Deliver*, 6:157–167 (1990); Jackson, *Analytical Biochem.*, 15:114–127 (1987)]. For conjugation with TMPEG, column purified AAV was dialyzed in 10 mM potassium phosphate buffer pH 7.4. Viral bands were desalted into 0.2 M sodium phosphate (pH 7.2) and 0.1 M sodium tetraborate (pH 9.2) buffers for conjugation reactions with SS-PEG and CC-PEG respectively. The inventors found that for conjugation by each type of PEG, a 10:1 (300 μg/3 mg) PEG:virus ratio (amt PEG:amt AAV protein) provided highly efficient reaction times and produced minimal loss of infectivity of the virus. AAV mixed with unactivated MPEG, a polymer that cannot covalently attach to the virus, served as a control for all in vitro and in vivo transduction experiments. All conjugation reactions were performed at room temperature under gentle stirring. Reactions were stopped by addition of a 10-fold excess (with respect to PEG concentration) L-lysine. Unreacted PEG, excess lysine, and reaction byproducts were eliminated by passing the preparation through a Sephadex G-50 column equilibrated with 10 mM potassium buffered saline (KPBS) pH 7.4. Fractions containing virus were identified by UV spectrophotometric analysis at 260 nm and pooled for further study.

EXAMPLE 2

Infectivity Assay for Conjugated and Unconjugated Virus

Aliquots of conjugated and unconjugated AAV were serially diluted in DMEM supplemented with 2% FBS and added to 293 cells. Two hours after infection, preparations were removed and replaced with complete medium. Twenty hours after infection, cells were washed with PBS, fixed with 0.5% glutaraldehyde, and washed twice with PBS containing 1 mM $MgCl_2$. β-galactosidase expression was determined by incubation with 1 mg/ml of the substrate, 5-bromo-4chloro-3-indolyl-β-galactoside (X-gal) in PBS containing 5 mM $K_3Fe(CN)_6$, 5 mM $K_4Fe(CN)_6 \cdot 3H_2O$, and 1 mM $MgCl_2$ for 2 hours at 37° C. in the dark. $Lac^+$ cells were coated from a minimum of 20 microscope fields. Percent infectivity was determined by calculating the ratio of the number of $Lac^+$ cells at various timepoints to the number of $Lac^+$ cells at the initiation of the study.

Unconjugated AAV experienced the most significant loss in titer (29%) over the entire reaction period. The CCPEG vector was the least stable of all the PEGylated preparations with losses similar to that of the native virus. Simple addition of PEG to a preparation does not compromise viral titer as addition of unactivated MPEG to the viral preparation did not significantly affect infectivity. Upon further investigation, it was found that the loss of infectivity of the CCPEG vector can be attributed to the formation of large aggregates due to crosslinking of multiple virions. However, reacting the vector with CCPEG for a shorter period of time yields fewer aggregates and even though less than 100% modification is achieved, transduction efficiency and stability are greatly enhanced.

EXAMPLE 3

Fluorescamine Assay

A fluorescamine assay was used to estimate the degree of modification of AAV capsids by activated polyethylene glycols. The assay was performed using a modification of established methods [Stocks, *Analytical Biochem.*, 154:232–234 (1986)]. Samples were taken 30, 60, 90, 120, and 480 minutes after initiation of the conjugation reaction. Serial dilutions were made from each sample in a volume of 1.5 ml of 10 mM sodium phosphate buffer pH 7.4. Fluorescamine (0.3 mg/ml, Sigma Chemicals, St. Louis, Mo.) in acetone (0.5 ml) was added to each dilution while vortexing. Fluorescence of the samples was measured on a spectrofluorimeter (Photon Technology International, Monmouth Junction, N.J.) with an excitation wavelength of 390 nm and emission at 475 nm. The resulting fluorescence is proportional to the concentration of free amino groups on the virus capsid. Standard curves were generated for each timepoint by plotting protein concentration versus fluorescent units. Degree of modification was obtained as the ratio between the slopes of conjugated and unconjugated viruses at similar timepoints.

TABLE 1

Degree of Modification for PEGylated AAV

| Time (minutes) | TMPEG | CCPEG | SSPEG |
| --- | --- | --- | --- |
| 0 | 0 | 0 | 0 |
| 15 | 95.8% | 78.9% | 100% |
| 30 | 100% | 85.25% | n.d. |
| 60 | n.d. | 100% | n.d. |

The reaction with CCPEG was complete after 60 minutes, a time when titer dropped by less than 10% and few aggregates had formed. Transduction efficiency of AAV was enhanced by conjugation with TMPEG over the entire reaction period. This reaction was complete in 30 minutes. Conjugation of AAV with SSPEG was complete within 15 minutes with minimal loss of titer over the entire reaction period.

EXAMPLE 4

Characterization of PEGylated AAV Preparations

Several physical tests were performed to confirm that activated PEG molecules were successfully conjugated to the AAV capsid.

A. Partitioning Assays

Partition coefficients of native and PEGylated viruses were determined as described previously [Delgado, *J. Biochem & Biophys, Meth.*, 22:237–250 (1994)]. Partitioning assays were performed at 25° C. in single microfuge tubes containing 1 g of a two-phase system of 4.75% (w/w) PEG 8000 (Sigma Chemicals, St. Louis, Mo.), and 4.75% Dextran T500 (Amersham Pharmacia Biotech, Piscataway, N.J.), in 0.15M NaCl containing 0.01 M sodium phosphate buffer, pH 6.8. The two phase system was prepared from stock solutions of 40% PEG, 20% dextran, 0.44M sodium phosphate buffer, pH 6.8 and 0.6M sodium chloride. AAV and PEGylated AAV were incorporated into the system by replacing 0.1 g of the water used to prepare the phases with 0.1 g of virus in coupling buffer. Samples were mixed 30–40 times by inversion and left to settle under gravity until complete separation of the phases was achieved. Aliquots from the top and bottom phases were analyzed for protein concentration by a microplate assay with Bio-Rad protein assay reagents and bovine serum albumin as a standard. The partition coefficient (K) is determined by the ratio between the protein concentrations in the top and bottom phases.

TABLE 2

AAV Partition Coefficients for PEGylated AAV

| AAV | Partition Coefficient |
| --- | --- |
| Unlabeled AAV | 0.68 |
| TMPEG | 1.37 |
| SSPEG | 1.01 |
| CCPEG | 1.26 |

Partitioning of the viral preparations in an aqueous two-phase system and calculation of partition coefficients (K) demonstrated that PEGylation modified the viral capsid significantly. K values shifted from 0.68 for unlabeled virus to 1.26 and 1.01 for CCPEG and SSPEG preparations, respectively. The TMPEG preparation demonstrated the highest level of conjugation with a K value of 1.37.

B. Zeta Potential

Zeta potential (electrophoretic mobility) of each PEGylated viral preparation was determined by laser Doppler anemometry (Zetasizer 3000, Malvern Instruments, Southboro, Mass.) in a thermostatized microelectrophoresis cell as described previously at a 1:25 dilution in 10 mM potassium phosphate buffer pH 7.4. Each reported value is the mean of three separate measurements.

The surface charge of the AAV capsid was effectively altered by the PEGylation process as zeta potential levels changed from −9.2 mV for native vector to −6.4 mV and −5.9 mV when conjugated to TMPEG and SSPEG, respectively. The CCPEG preparation demonstrated the greatest shift toward neutrality to −5.1 mV.

C. Electron Microscopy

Aliquots of conjugated viral particles were fixed in 1% glutaraldehyde, 0.05M cacodylate buffer pH 7.4 for 10 min at room temperature. The solution was spread over 200-mesh carbon-coated grids (Electron Microscopy Sciences, Fort Washington, Pa.). After 10 min excess suspension was wicked off grids with filter paper. The grids were stained with 2% uranyl acetate for 1 min, rinsed, and allowed to dry. Viral particles were viewed using a Philips CM-10 transmission electron microscope (Eindhoven, The Netherlands).

The average particle size for PEGylated AAV in three separate animal studies is provided in the following table.

$\mu$l of DMEM supplemented with 20% FBS was added to each well. Cells are incubated for 24 hours and the expression of green fluorescence protein (GFP) measured by FluoroImaging (Molecular Dynamics). NAB titers are calculated as the highest dilution at which 50% of the cells stained green.

Anti-AAV NAB was reduced following administration of TMPEG and SSPEG conjugated vector by 20% and 50% respectively. The CCPEG preparation was the least efficient

TABLE 3

PARTICLE SIZE DATA FOR PEGylated AAV

| AAV | Unlabeled starting material | TMPEG | SSPEG (99.9%) | CCPEG | MPEG unactivated PEG |
|---|---|---|---|---|---|
| W257 and W260 | 289.1 ± 129.81 (72.1%) | 634.4 ± 102.3 (100%) | 13.05 ± 1.18 | 150.52 ± 62.06 (77.8%) | — |
| | 2922.7 ± 240.31 (11.8%) | | 607.72 ± 232.38 (0.1%) | 2991.87 ± 152.53 (4.1%) | |
| | 5078.5 ± 384.47 (16.1%) | | | 5093.17 ± 374.08 (7.3%) | |
| W259 | 262.8 ± 117.42 (100%) | 299.4 ± 73.81 (100%) | 17.08 ± 3.47 (99.9%) | 326.2 ± 151.93 (90.4%) | — |
| | | | 313.0 ± 150.41 (0.1%) | 5137.5 ± 314.97 (9.6%) | |
| W267 | 135.2 ± 5.84 (2.3%) | 120.1 ± 12.54 (84.5%) | 17.64 ± 4.25 (99.9%) | 328.1 ± 140.77 (58.5%) | 1003.6 ± 201.2 (24.4%) |
| | 1200.2 ± 645.27 (90.1%) | 703.1 ± 307.46 (8.0%) | 290.12 ± 155.06 (0.1%) | 2908.8 ± 271.58 (20.2%) | 1468.7 ± 47.4 (9.6%) |
| | 4820.1 ± 647.96 (7.5%) | 2863.2 ± 262.86 (7.5%) | | 5069.0 ± 390.66 (21.4%) | 2908.9 ± 289.86 (66.0%) |

EXAMPLE 5

Neutralization Assays

In order to determine if the PEG-modification process of the invention (i.e., "pegylation") could preserve AAV transduction efficiency in the presence of neutralizing antibodies (NAB), conjugated AAV preparations were incubated in the presence of serum from C57BL/6 mice previously given multiple doses of AAV ($1 \times 10^{12}$ particles) or serum from non-immunized C57BL/6 mice.

Two hundred microliter aliquots (equivalent to a multiplicity of infection of 50) was applied to 84-31 cells (a 293-based E1/E4 complementing cell line) in triplicate. After a 2 hour incubation, vector is replaced with complete medium. Forty-eight hours after infection, cells are washed with PBS, fixed for 10 min in 0.5% glutaraldehyde, and washed twice with PBS containing 1 mM $MgCl_2$. Transduction levels are reported as the ratio of cells transduced by virus incubated with immune serum to cells transduced by virus incubated with non-immune serum.

Transduction efficiencies of the PEGylated vectors were unaffected by the presence of immune serum at a 1:100 and 1:1000 dilution while that of the unconjugated preparation diminished by 49% and 32%, respectively. At the highest dilution, transduction efficiencies of PEGylated vectors fell by approximately 30% but were significantly higher than that of the unconjugated virus (Student's t-test, $p \leq 0.01$).

Mouse serum was analyzed for NAB by incubation at 56° C. for 30 min to inactivate complement followed by dilution in DMEM in twofold increments starting from a 1:20 dilution. Each dilution (100 $\mu$l) is mixed with virus, incubated for 1 hour at 37° C., and applied to 84-31 cells in 96-well plates ($2 \times 10^4$ cells/well). After 1 hour at 37° C., 100 vector for this application with transgene levels falling 10-fold below the other vectors at all timepoints and to undetectable levels 60 days after injection. NAB levels were only modestly reduced by this preparation.

EXAMPLE 6

Administration of PEG-Modified Vectors to Immunocompetent Animals

The following study demonstrates that PEGylation according to the present invention does not affect transduction efficiency of AAV when administered to the muscle or liver of immunocompetent animals.

C57BL/6 ($H-2^b$) mice (6–8 weeks old) were purchased from Jackson Laboratories (Bar Harbor, Me.). To determine the effect of PEGylaton has on AV transduction, unconjugated native AAValbα1AT or AAVCMVlacZ, the same viruses conjugated with various polyethylene glycols as described above and virus mixed with unactivated MPEG were administered either intramuscularly ($5 \times 10^{10}$ particles in 50 $\mu$l PBS) or into the liver ($1 \times 10^{11}$ particles in 100 $\mu$l PBS). Animals were necropsied 14 days post-injection and tissues divided with half rapidly immersed in peel-away molds containing OTC compound (Miles Diagnostics, Ekhart, Ind.) and flash frozen in a dry ice/isopentane bath for cryosectioning. Remaining tissue was placed in cold DMEM and processed for assay of expression as described below.

A. β-gal Assays

Treated tissues are excised from freshly euthanized animals and washed twice in cold PBS. When numerous samples are processed, excised tissues are stored no longer than 2 hours in cold DMEM. Tissues are rinsed in lysis buffer (provided with the β-gal ELISA kit, Boehringer- Mannheim) containing 4 mM Pefablock (Boehringer-Mannheim), 1 mM phenylmethylsultonyl fluoride (PMSF), 1 mM benzamidine, 1 μg/ml pepstatin, 5 μg/ml aprotinin (Sigma), 1 μg/ml leupeptin, 0.5 mM EDTA, and 0.5 mM dithiothreitol (DTT). Tissues are homogenized in 1 ml of lysis buffer using a Brinkman polytron. Following homogenization, extracts are centrifuged at 14,000 rpm for 10 minutes. The protein concentration of the cleared supernatants was determined by a microplate assay with Bio-Rad DC Protein assay reagents and bovine serum albumin as a standard. Extracts were quick-frozen in a dry ice/ethanol bath and stored at −80° C. until assayed. β-gal concentrations are determined by an enzyme-linked immunosorbent assay (ELISA) using a β-gal ELISA kit (Boehringer-Mannheim) according to manufacturer's instructions.

After intramuscular injection of an AAVCMVlacZ vector, initial transduction efficiency of the TMPEG, SSPEG and unconjugated virions were not statistically significant (Student's t-test, $p \leq 0.05$); in each case transgene expression was generally stable during the period of the experiment. The CCPEG preparation was the least efficient and produced transgene levels that were reduced 10-fold below the other vectors at each time point, with gene expression dropping to undetectable levels 60 days after injection. All animals that received intramuscular injection of either the native or the conjugated preparations developed high levels of neutralizing antibody against AAV capsid proteins.

B. Human Alpha-1 Antitrypsin Assay

Concentration of human α1AT in mouse serum was determined by an enzyme-linked immunosorbent assay (ELISA) as described previously [W. D. Xiao et al, *J. Virol.*, 73:3994–4003 (1999)]. Microtiter plates (MaxiSorp, Nunc) were coated with 100 μl rabbit anti-human α1AT antibody (1:100, Sigma) at 4° C. overnight, blocked and incubated with standards or samples overnight at 4° C. After washing, the primary antibody (1:1000, goat anti-human α1AT, Sigma) was incubated with the captured antigen for two hours at room temperature. Secondary antibody (anti-goat IgG-peroxidase conjugate, Sigma, 1:10,000) was added for 2 hours at room temperature. ABTS reagent (Boehringer Mannheim) was added and concentration determined from absorbance readings at 405 nm. The sensitivity of the assay is 0.3 to 30 ng/ml.

When animals were injected intravenously with an AAValbα1AT vector, TMPEG and SSPEG preparations only differed from the native vector by the rate at which gene expression plateaued. A peak level of gene expression equal to $1 \times 10^4$ ng/ml of α1AT was noted for native vector as well as SSPEG and TMPEG conjugated vector when evaluated 14 days after injection.

EXAMPLE 7

Analysis of AAV-specific, Immunoglobulins

Serum samples from mice were assessed for AAV-specific isotype specific immunoglobulins (IgG1, IgG2a, IgG2b, IgG3, IgM) by ELISA as described previously [N. Chirmule, et al, *J. Immunol.*, 163:448–455 (1999)]. Microtiter plates (MaxiSorp, Nunc) were coated with 100 μl AAV antigen ($5 \times 10^{10}$ particles/ml) in 0.1 bicarbonate buffer, pH 9.6 overnight at 4° C., washed four times with PBS containing 0.05% Tween 20 and blocked in PBS containing 3% BSA for three hours at room temperature. Serum samples at a 1:100 dilution were added to the antigen-coated plates and incubated overnight at 4° C. Plates were washed four times with PBS containing 0.05% Tween 20 and incubated with biotin conjugated rat anti-mouse anti-IgG1, IgG2a, IgG2b, IgG3, IgM (PharMingen, San Diego, Calif.) at a 1:1000 dilution for three hours at room temperature. Plates were washed as above and a 1:10,000 dilution of alkaline phosphatase conjugated avidin (Sigma Chemical Company, St. Louis, Mo.) was added for two hours at room temperature. After four washings, p-nitrophenyl phosphate in diethanolamine buffer was added (Sigma Chemical Company, St. Louis, Mo.) and optical densities read at 405 mn on a microplate reader (Dynatech Laboratories, Chantilly, Va.).

Characterization of the anti-AAV antibody isotypes revealed this was the case as the CCPEG preparation was the only formulation to significantly enhance production of IgG1 antibodies, those associated with the Th2 pathway.

EXAMPLE 8

Immunization Experiments

Results from immunization studies using rAAV which has been pegylated according to the present invention demonstrates that the pegylated rAAV of the invention permit enhanced gene expression.

A. PEGylation Allows for Significant Gene Expression In Immunocompetent Animals After Prior Exposure to the Native Vector As shown herein, transduction efficiency of some PEGylated vectors is not affected by the presence of neutralizing antibodies (NABs) to native vector in vitro. In order to determine if this effect could also occur in vivo, animals were challenged with a second dose of PEGylated vector ($1 \times 10^{11}$ particles i.v. or $5 \times 10^{10}$ particles i.m.) 30 days after initial immunization with the same dose of native AAV. The second vector was AAVCMVlacZ for intramuscular injections and AAValbα1AT for intravenous infusions. Animals that received two doses of native vector intramuscularly did not demonstrate significant levels of gene expression upon rechallenge. Animals that received the TMPEG preparation had significant levels of gene transduction upon readministration, although it was reduced approximately 7.5-fold as compared to naïve animals. The level of gene expression, obtained with SSPEG preparation was substantial but 10-fold lower than naïve animals. A significant level of gene expression was also seen with the CCPEG preparation, but this was the least effective.

Administration of two doses of native AAV intravenously failed to produce significant levels of gene expression following the second vector. All PEGylated preparations delivered intravenously yielded high levels of gene transfer following intravenous immunization with native vector that were similar to that observed in naïve animals ranging from 100% of naive for TMPEG to 40% of native for CCPEG.

B. PEGylation Allows for Significant Gene Expression by Unconjugated AAV In Immunocompetent Animals After Prior Exposure to PEGylated Virus The impact of humoral immune responses to PEGylated vectors on gene transfer with native virus was studied. Mice immunized with different preparations of PEGylated AAV were given a second intramuscular injection of $5 \times 10^{10}$ particles of the native vector. Significant levels of gene expression were detected in animals immunized with CCPEG and SSPEG preparations, despite the presence of anti-AAV antibodies. Mice immunized with the TMPEG preparation produced the most significant levels of gene expression upon rechallenge with native virus, but were still somewhat below those seen in naïve animals.

Native virus directed to liver produced significant levels of gene expression in animals immunized intravenously with PEGylated AAV. Mice immunized with SSPEG and CCPEG preparations demonstrated significant levels of gene expression upon readministration, as measured by α1AT serum levels, that were only 42% (SSPEG) and 21% (CCPEG) lower than that seen from a single dose of vector administered to naïve animals. Native vector produced the most significant level of gene expression in animals immunized with TMPEG despite the fact that those animals had the highest levels of NAB to native vector prior to administration.

C. Repeated Administration of PEGylated AAV Produces Significant Levels of Gene Expression in Liver but Not in Muscle C57BL/6 received two consecutive intramuscular doses of PEGylated AAV. The goal of these experiments were to evaluate gene transfer efficiency with a particular form of PEGylated AAV following a previous immunization with the same type of PEGylated vector. Readministration of the same type of PEGylated vector was substantially reduced when compared to an intramuscular injection into naïve animals for each PEGylated vector ranging from a 20-fold reduction with CCPEG, to a 200-fold reduction with SSPEG. All animals developed significant titers of anti-AAV NAB. When administered intravenously, gene expression after two doses of the CCPEG preparation produced α1AT serum levels equivalent to those seen in naïve animals, despite the presence of anti-AAV NAB. The SSPEG preparation produced slightly reduced gene expression after readministration (i.e., 50% of naïve animals). Transduction of the TMPEG preparation upon readministration surpassed that of naïve animals.

EXAMPLE 9

Production of Conjugated Adenoviral Vectors

E1/E3-deleted adenoviral vectors expressing β-galactosidase (H5.010.CMV.LacZ) were used for these studies and were amplified in 293 cells using a modification of established methods and purified from cell lysates by banding twice on CsCl gradients (Graham and Van der, Virology, 52:456–467 (1973)]. Aliquots of virus were desalted on Econo-Pac 10DG disposable chromatography columns (Bio-Rad, Hercules, Calif.) and equilibrated with the respective buffer for optimal conjugation (see below). Viral concentrations were determined by UV spectrophotometric analysis at 260 nm. Transduction titer (i.e., LacZ forming units or lfu) was determined by limiting dilution infections of 293 cells. The particle/lfu ratio of both conjugated and unconjugated virus was approximately 100. Protein content of Ad preparations was determined by a microplate assay with Bio-Rad DC Protein assay reagents and bovine serum albumin as a standard.

These adenoviral vectors were conjugated with the three types of activated PEG as described in Example 1B.

EXAMPLE 10

Conjugation of activated MPEGs to adenoviral capsids occurs rapidly with minimal loss of viral infectivity The TMPEG-adenovirus (Ad) preparation retained viral titer over the entire reaction period while the SSPEG preparation lost 70% of the original titer when the conjugation reaction was complete. Premature termination of the SSPEG reaction (i.e., at 75 minutes when it was 70% complete) resulted in a preparation with 90% residual activity. Modification of the virus with CCPEG was complete in 90 minutes, however, only 11% of the original infectivity remained. Fractionation of this preparation over a Sephadex G50 column produced distinct viral populations. The first peak represented PEGylated monomer virus with high infectivity while the second peak contained aggregated virus (per electron microscopy and static laser light scatter, data not shown) with low activity. Only the first peak was isolated and used in additional studies. Addition of unactivated MPEG to Ad preparations had no effect on infectivity as compared to vector in buffer alone (data not shown).

Significant loss of titer with CCPEG can be attributed to the production of large viral aggregates due to extensive cross-linking of the polymer with viral capsids. This is manufactured as a mixture of two isoforms, one that will attach to proteins by a single amide bond, and another that is capable of forming two amide bonds with the target protein. Once aggregates were removed, the remaining viral suspension proved to be highly infectious and extremely stable under various storage conditions. The SSPEG preparation also experienced a significant drop in titer after conjugation for one hour at room temperature. No aggregation phenomena was detected with this compound, however, loss in titer could be attributed to attachment of multiple SSPEG molecules to a single lysine residue. In order to maintain substantial viral infectivity with significant modification, a reaction time of 75 minutes, which modified 70% of available lysine residues and maintained titer was selected. While this was the only protocol that did not completely modify the viral capsid, the resultant vector could efficiently evade neutralization by immune serum and maintained the highest titers at the various storage conditions with respect to the other PEGylated preparations. These data indicate that complete modification of the viral capsid with this polymer is not a strict requirement for production of highly efficient viral vectors.

EXAMPLE 11

Characterization of Ad-PEG Complexes

Several physical tests were performed to confirm that activated PEG molecules were successfully conjugated to the adenovirus capsid. Partitioning assays and zeta potential were performed as described in Example 4.

Partitioning of the viral preparations in an aqueous two-phase system and calculation of partition coefficients (K) demonstrated that the viral capsid was significantly modified. K values shifted from 0.7 for unlabeled virus to 1.76 and 1.96 for TMPEG and SSPEG preparations, respectively. The CCPEG preparation demonstrated the highest level of conjugation with a K value of 3.56.

Zeta potential analysis revealed that surface charge of the adenovirus capsid significantly changed from −48.1 mV to −27.8 and −24.2 mV when conjugated to TMPEG and SSPEG respectively. The CCPEG preparation demonstrated the greatest shift toward neutrality to −16.2 mV.

EXAMPLE 12

Adenovirus-PEG Complexes are Protected from Neutralization by Immune Serum

PEGylated preparations were added to HeLa cells in the presence of neutralizing antibodies to adenovirus capsid proteins and transduction levels were compared to that of the same preparation incubated in non-immune serum. This study was performed essentially as described in Example 5 above, with the exception that the immune serum was derived from C57BL/6 mice harvested 28 days after intravenous injection of adenovirus vector.

Transduction efficiency of the unconjugated virus was significantly reduced by neutralizing antibodies. The TMPEG preparation did shield the virus partially from neutralization while transduction of the SSPEG and CCPEG preparations was unaffected by the presence of neutralizing antibody.

EXAMPLE 13

Stability of PEGylated Adenoviruses

As shown in the study below, MPEG, when added at a concentration similar to that employed in the PEGylation reaction, extended viral stability at 42° C. and 25° C. beyond that of the unconjugated adenovirus, but viral titers were substantially lower than those of the PEGylated virions. Precipitates were eventually detected in these preparations which significantly contributed to losses in transduction. However, addition of this excipient to adenovirus formulations at 4° C. significantly enhanced stability beyond that of the native virus for up to five months due to its ability to maintain capsid assembly at this temperature. Addition of glycerol to PEGylated preparations did not affect the stability of the virus at −20° C. This result is encouraging as glycerol (and its associated toxicity) can be eliminated from preparations for clinical use. While each PEGylated preparation lost about 1 log of titer over four months, they were stored in the absence of any additional cryoprotectants. Addition of carbohydrates, surfactants and other stabilizers will enhance stability and reduce loss in titer to negligible levels.

A. PEGylated Adenoviruses are Significantly More Stable Under Various Storage Conditions than Unconjugated Virus The ability of PEGylation to stabilize virus at a wide variety of temperatures was assessed. Preparations were stored in potassium buffered saline (KPBS) with or without the addition of 10% glycerol at −20° C. and at 4° C. Unconjugated adenovirus suffered a drop in titer of one log after storage at 4° C. for eight hours, falling to undetectable levels seven days after storage. This rapid degradation of viral capsids is readily detected by electron microscopy. After 24 hours at 4° C., the unconjugated viral preparation consists mainly of single viral capsid proteins, mostly hexons; only a few intact viral particles could be detected. The CCPEG preparation was the least stable of the remaining preparations as titer fell one log after incubation at 4° C. for 24 hours. Electron micrographs display unequivocal evidence that this preparation is significantly more stable than unconjugated virus as photos taken at twelve days after storage reveal intact virions. TMPEG preparations demonstrated a negligible loss in titer at 4° C. for one week; after 42 days, titer fell by two logs and remained at this level for the duration of the study. At this time, the preparation mainly consisted of intact viral capsids with only a few compromised virions. The SSPEG preparation underwent an initial drop in titer of one log after eight hours at 4° C. and maintained titer for up to 150 days. This preparation was indistinguishable from freshly purified virions upon inspection by electron microscopy 120 days after storage at 4° C.

Stability studies of PEGylated preparations at −20° C. revealed that the addition of glycerol was not necessary for maintenance of titer. In the absence of glycerol, titers of unconjugated virions dropped 5.5 logs after 15 days at −20° C. in KPBS. Degradation of the virus steadily continued at the rate of 1 log/month for the remainder of the study. Addition of 10% glycerol significantly enhanced stability as only one log unit of titer was lost in the unconjugated preparations stored at −20° C. over four months. SSPEG conjugated virions were the most stable of all the preparations studied with a drop in titer of 0.8 log over 120 days at −20° C.; addition of glycerol only slightly enhanced stability. Titer of the TMPEG preparation was the most sensitive to the addition of glycerol. The preparation without glycerol demonstrated a drop of one log after 90 days in storage, while the titer of the preparation that contained glycerol dropped only 0.5 log unit. CCPEG virions were least stable with a 4 log decrease of infectious virus after 90 days of storage at −20° C.; glycerol did not help.

B. PEGylation Enhances Adenoviral Stability under Extreme Storage Conditions

Even though the stability data for PEGylated viral preparations at 4° C. and −20° C. was very encouraging, these conditions would still require shipment on ice to various clinical sites. In order to assess the possibility of vector shipment under ambient conditions, samples were stored in KPBS at 25° C. and at 42° C. Upon storage at 25° C., unconjugated adenovirus dropped in titer at a rate of 1 log/day. Addition of monomethoxy poly(ethylene) glycol to the adenovirus preparation slightly enhanced stability of unconjugated adenoviral preparations with the loss of titer at an average rate of 0.6 log units/day.

CCPEG preparations were very stable at room temperature. An initial drop in titer from $5.84 \times 10^{10}$ lfu/ml to $3.18 \times 10^{10}$ lfu/ml was detected after six hours, which subsequently stabilized for one week. TMPEG preparations were stable for 24 hours while titer of the SSPEG preparation remained constant for up to five days, which would allow for priority shipment of vector in the absence of dry ice. When stored at 42° C., titer of unconjugated adenovirus preparations initially fell at a steady rate of approximately 1 log every 45 minutes. Addition of inactivated MPEG delayed the loss, which did eventually diminish two logs over three hours. TMPEG and CCPEG preparations demonstrated similar degradation rates with titers falling 1.5 log units over the study period. The SSPEG preparation was the most stable with negligible loss of titer for 18 hours at this condition. The SSPEG preparation demonstrated a negligible loss of titer at 42° C. for up to eight hours. Thus, this preparation could survive exposure to extreme temperatures upon shipping without significant loss of titer.

EXAMPLE 14

Administration of PEGylated Adenoviral Vectors to Immunocompetent Animals

C57BL/6 (H-$2^b$) mice (6–8 weeks old) were purchased from Jackson Laboratories (Bar Harbor, Me.). Preparations were administered either via the tail vein ($1 \times 10^{11}$ particles in 100 $\mu$l KPBS) or intratracheally ($5 \times 10^{10}$ particles in 50 $\mu$l KPBS). Animals were necropsied four days later and excised tissues washed twice in cold PBS and stored in cold DMEM for processing. Tissues were homogenized in 1 ml of lysis buffer using a Brinkman polytron. Extracts were centrifuged at 14,000 rpm for ten minutes. Protein concentration of supernatants was determined with Bio-Rad DC Protein assay reagents and bovine serum albumin as a standard. Extracts were quick-frozen in dry ice and stored at −80° C. until assayed. β-gal concentrations were determined with a β-gal ELISA kit (Boehringer-Mannheim) according to manufacturer's instructions.

When administered to the lung, unconjugated virus produced $1.42 \times 10^4 \pm 3.6 \times 10^3$ pg of β-galactosidase/mg protein. The CCPEG and SSPEG preparations produced β-galactosidase expression levels two fold higher than unconjugated virus. The TMPEG preparation demonstrated the largest increase in transduction with a 2.5-fold increase in beta-galactosidase. Addition of inactivated MPEG to Ad preparations raised transduction to a level three times that of the unconjugated virus.

Administration of unconjugated adenovirus intravenously yielded beta-galactosidase levels of $3.0 \times 10^6 \pm 1.1 \times 10^5$ pg/mg of protein in the liver. In vivo transduction of liver was 6-fold higher with TMPEG, CCPEG and SSPEG. Addition of MPEG to the viral preparation slightly raised transduction levels beyond that of the unconjugated virus.

PEGylation of adenoviral vectors enhanced transduction efficiency when administered intratracheally or intravenously. This effect was somewhat unexpected as the majority of lysine residues that are present on the viral capsid are concentrated on the fiber and penton proteins which are necessary for viral binding and entry into target cells [(Adam, et al., *Acta Microbiologica Academiae Scientiarum Hungaricae*, 24:181–187 (1977), Bergelson, et al., *Science*, 275:1320–1323 (1997), Wickham, et al., *Cell*, 73:309–319 (1993)]. However, the new physical characteristics of the PEGylated viruses may contribute to the observed increase in viral transduction. Zeta potential measurements have shown that the adenovirus bears a significant negative charge on the capsid. Surface charge of viral vectors can significantly affect the level of transduction in various target tissues (Fasbender, et al., *J. Biol. Chem.*, 272:6479–6489 (1997)]. It has been found that adenoviral transduction is inhibited due to static repulsion between the negatively charged sialic acid residues on the cell surface and the virus (Arcasoy, et al., *Am. J. Resp. Cell & Molec. Biol.*, 17:422–435 (1997)]. PEGylation effectively masks the groups responsible for this charge, producing an environment that would favor non-specific interaction of the virus with the cell membrane. Particle size measurements of the final PEGylated preparations also revealed that each method produced a suspension of single viral particles which enhance the number of virions that come in contact with cell monolayers and, as a result, can increase transduction efficiency. Partition coefficients for the PEGylated virions indicate that the modified vectors have an increased affinity for hydrophobic environ-ments that would allow for an increased ability to indiscreetly partition through cell membranes. Initial studies to assess the mechanism by which transduction efficiency of PEGylated adenoviruses is enhanced supports this theory as permeability of the PEGylated vectors across differentiated monolayers is significantly enhanced (data not shown).

EXAMPLE 15

Assessment of Formulations for Use in Frozen and Lyophilized Viral Preparations Two buffers that are acceptable for human use, 10 mM sodium phosphate (DPBS) and 10 mM potassium phosphate (KPBS) buffered saline, were assessed for their ability to maintain pH at low temperature.

A. Effect of Temperature on Various Formulations

Materials: Sucrose USP, beta cyclodextrin, D-mannitol USP, D(+) trehalose, sorbitan monolaurate (Span 20), and phosphate-buffered saline (PBS) were purchased from Sigma (St. Louis, Mo.). Potassium dihydrogen phosphate ($KH_2PO_4$), dipotassium hydrogen phosphate ($K_2HPO_4$), and potassium chloride USP were purchased from J T Baker (Phillipsburg, N.J.). Glycerol USP was purchased from EM Science (Gibbstown, N.J.). Tertiary amine beta cyclodextrin was purchased from Cerestar USA, Inc. (Hammond Ind.). Pluronic block copolymer F68 was kindly provided by the BASF corporation (Mt. Olive, N.J.). Universal pH Indicator was purchased from Fisher Scientific (Pittsburgh, Pa.).

Sample Preparation: All formulations were prepared under GLP conditions and sterilized by filtration through a 0.22 μm filter (Corning). For all studies, 250–1000 μl aliquots were added to autoclaved 3 ml clear borosilicate glass vials (Wheaton, Millville, N.J.). Vials were topped with 13 mm gray butyl rubber stoppers (Wheaton) and sealed with tear-off aluminum seals (Wheaton). For pH studies, 10 μl of Universal pH Indicator was added to monitor pH changes during freezing.

pH Studies: Eight samples were prepared for each formulation as described. Four samples contained Universal pH indicator [M. A. Croyle et al, *Pharm. Dev. Technol.*, 3(3): 373–383 (1998); S. Nema and K. E. Avis, *J. Parenteral Science & Technology*, 47(2):76–83 (1993)]. The remaining samples did not contain the indicator and were used to determine viral titer after freezing. Samples were frozen for 12 hours at −20 and −80° C. pH of the frozen products were determined visually and noted for each formulation. Samples not containing indicator were slowly warmed to 25° C. and assessed for viral potency. The results are shown in Table 4 below.

TABLE 4

| Formulation | KPBS (pH) | | DPBS (pH) | |
|---|---|---|---|---|
| | −20° C. | −80° C. | −20° C. | −80° C. |
| Buffer alone | 6.0 | 4.5 | 5.0 | 4.0 |
| Glycerol | 6.0 | 6.5 | 5.0 | 5.0 |
| 0.25M Sucrose | 6.0 | 4.0 | 5.0 | 4.0 |
| 0.5M Sucrose | 6.0 | 4.0 | 5.5 | 4.0 |
| 1.0M Sucrose | 6.5 | 5.5 | 6.0 | 4.0 |
| 0.25M Trehalose | 6.0 | 4.0 | 5.5 | 4.0 |
| 0.5M Trehalose | 6.0 | 4.0 | 5.5 | 4.0 |
| 1.0M Trehalose | 6.0 | 5.0 | 6.0 | 4.0 |
| 0.5% BCD | 6.5 | 6.0 | 5.5 | 5.5 |
| 5% TMBCD | 7.4 | 7.4 | 7.4 | 7.4 | pH of sodium phosphate buffered saline dropped from pH 7.4 to 5.0 when frozen at −20° C. and to pH 4 at −80° C. (see Table above). Addition of glycerol to the buffer did not prevent the drop in pH upon freezing. Differential scanning calorimetry demonstrated that this change in pH is associated with precipitation of buffer components during freezing. Addition of sucrose or trehalose to the buffer could not prevent this phenomenon at −80° C., but each sugar at a 1M concentration did prevent dramatic pH changes at −20° C. Potassium phosphate buffer did not demonstrate the significant changes in pH as seen with the sodium phosphate buffer (DPBS) at −20° C., but did experience similar drops in pH at −80° C. Addition of cryoprotectants did not significantly affect the final pH of the preparation. However, it is important to note that for each buffer system, tertiary amine beta cyclodextrin (TMBCD) could maintain physiological pH upon freezing.

B. Effect of Temperature on Various Formulation Containing Viral Vectors

Virus was formulated in the following manner and frozen at the respective temperature for 12 hours. Samples were thawed at 25° C. and viral titer assessed in order to determine if change in pH would significantly affect physical stability.

As used throughout the following examples, the term lac-forming unit (lfu) defines the number of infectious viral particles present in a preparation of beta-galactosidase (lacZ) expressing virus as measured by limiting dilution, infection of 293 cells [or 84-31 cells, a cell line expressing adenovirus E1 and E4 in the case of AAV (K. J. Fisher et al, *J. Virol.*, 70:520–532 (1996))], histochemical staining and visual identification of lac$^+$ cells. Samples were serially diluted in DMEM supplemented with 2% fetal bovine serum. Medium was removed from 12 well plates seeded with $1.5 \times 10^4$ cells/well and 0.2 ml of the appropriate dilution was placed on the monolayers. After two hours at 37° C., 2 ml of complete medium was added to each well and the infection continued for 16 hours at 37° C. At this time, medium was removed and cells stained for beta-galactosidase expression as described previously [M. A. Croyle, et al, *Pharm. Dev. Technol.*, 3(3):365–372 (1998)]. Lac$^+$ cells were tallied from a minimum of 20 microscope fields (approximately 48,000 cells). Lac-forming units were calculated as described previously [M. A. Croyle et al, *Pharm Dev Technol*, 3(3):373–383 (1998)]. The sensitivity of the assay was 10 to $1 \times 10^{12}$ lfu/ml.

1. Preparation of Adenovirus

First-generation adenovirus expressing *E. coli* β-galactosidase under the control of a CMV promoter was amplified in 293 cells using a modification of established methods [F. L. Graham and A. J. van der Eb, *Virology*, 52:456–467 (1973)]. Virus was purified from cell lysates by banding twice on CsCl gradients followed by desalting on Econo-Pac 10DG disposable chromatography columns (Bio-Rad, Hercules, Calif.) equilibrated with each respective formulation. Concentration of the virus was determined by UV spectrophotometric analysis at 260 nm and lac-forming assays. All experiments were performed with freshly purified adenovirus.

2. Preparation of Adeno-Associated Virus

Production of recombinant AAV2 expressing the *E. coli* beta-galactosidase gene under the control of a CMV promoter involved transfecting 60% confluent 293 cells in 150 mm dishes with a 1:1:2 ratio of cis plasmid (pAAVlacZ, with AAV ITRs), trans plasmid (p5E18, containing AAV2 Rep and AAV1 Cap [W. Xiao et al, *J. Virol.*, 73(5):3994–4003 (1999)]) and helper plasmid (pfΔ13, an adenovirus plasmid with most of the late genes deleted and an 8 kb deletion in the E2b region). Transfection was performed by calcium phosphate precipitation. Ninety-six hours after transfection, cells were harvested and subjected to two rounds of CsCl gradient purification as described previously [K. J. Fisher et al, *Nature Medicine*, 3:306–312 (1997)]. Virus was desalted by dialysis against respective formulations.

3. Results

Figure 1B:
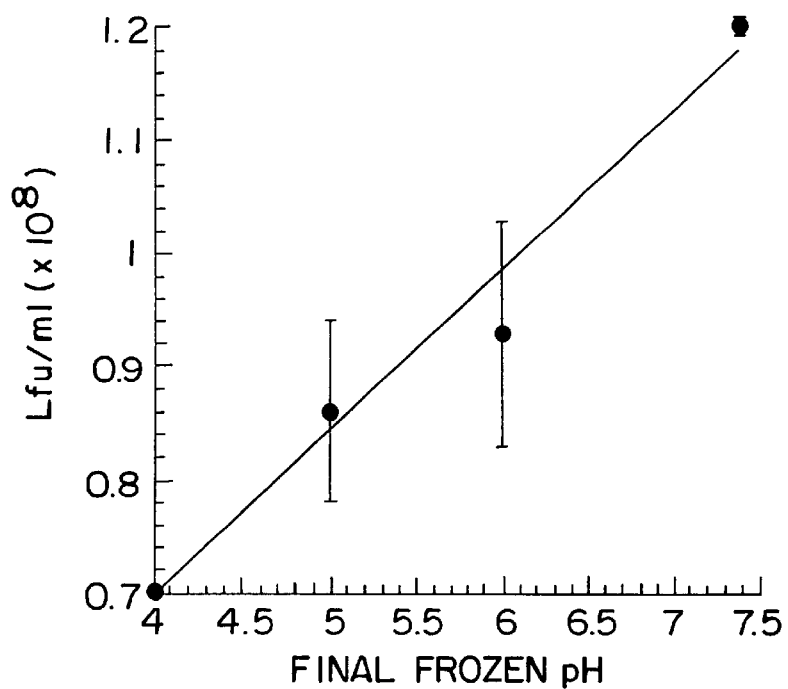
FIG. 1B illustrates the results of a study on the effect of the final frozen pH of a formulation on adeno-associated virus stability (correlation coefficient, $r^2=0.98$). See Example 15. The results are reported as the average titer of 4–6 samples from two separate experiments. Error bars reflect the standard deviation of the data.
Figure 1C:
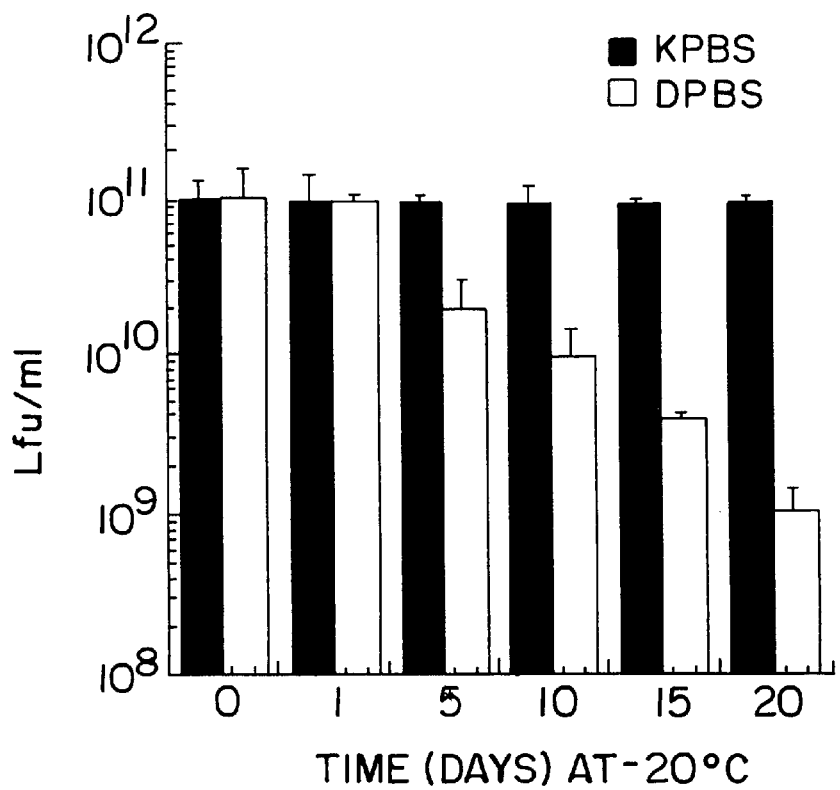
FIG. 1C illustrates the results of a study of the stability of adenovirus prepared in either sodium (DPBS) or potassium (KPBS) phosphate buffered saline and 10% glycerol at $-20°$ C.

Adenoviral preparations were quite sensitive to pH changes upon freezing (FIG. 1A). Preparations that maintained initial pH (7.4) did not experience significant drops in titer upon thawing. Preparations that underwent a drop of 3 pH units suffered a one log loss of titer. Adeno-associated virus (AAV) was not as sensitive to pH changes upon freezing as the adenovirus (FIG. 1B). AAV preparations that experienced a drop of 3 pH units upon freezing lost 0.5 log of infectious virus. As stated above, potassium phosphate buffered saline maintained pH to a higher degree than sodium phosphate buffered saline when frozen at –20° C. Adenovirus stored in 10% glycerol in this buffer system demonstrated superior stability over sodium phosphate buffered preparations. As a result, potassium phosphate buffered saline was the buffer of choice for all formulations unless otherwise indicated.

EXAMPLE 16

Stability of Adenoviral Formulations at –20° C. and 4° C.

After screening potential formulations and buffer systems for the ability to maintain pH at low temperature, large scale preparations of formulated virus were stored at –20 and 4° C. for a period of two years. Prior to storage, viral titer was determined by lac-forming assay (t=0). In order to assess the real-time stability of vector in each formulation, 4–6 vials from each lot were removed and assessed for transduction efficiency. Viral titer of each formulation was compared to titer from virus produced in the same lot stored at –20° C. in KPBS. Expiration dates were assigned to each preparation at the time when titer fell to 90% of its original value (i.e. suffered 10% loss (0.1 log)) as is standard practice in the pharmaceutical industry [Carstensen, J. T., Drug Stability: Principles and Practices. Second Edition, *Drugs and the Pharmaceutical Sciences*, Vol. 68. 1995, New York, N.Y.: Marcel Dekker, Inc.; International Conference on Harmonization (ICH), *Harmonized Tripartite Guideline, Stability Testing of New Drug Substances and Products*, 1993; Center for Drugs and Biologics FDA, Guidelines (1987): *Guideline for Submitting Documentation for the Stability of Human Drugs and Biologics*, 1987: Rockville, Md.].

TABLE 5

Expiration Dates for Adenoviral Formulations Stored at –20° C.

| Formulation | Expiration |
| --- | --- |
| 1M Sucrose/KPBS/5% TMBCD | 690 days |
| 1M Sucrose/KPBS/0.5% BCD | 360 days |
| 1M Sucrose/KPBS | 70 days |
| 1M Sucrose/DPBS/5% TMBCD | 45 days |
| 0.5M SucroseIKPBS | 18 days |
| 10% Glycerol/KPBS | 12 days |
| 10% Glycerol/DPBS | 2 days |
| DPBS | 12 hours |

Glycerol preparations were the least stable at –20° C. The sodium phosphate buffered preparation lost 10% of the original titer in 2 days (Table 5). Potassium phosphate buffer extended the shelf life of the virus to 12 days. When glycerol was removed and sucrose added to the preparation, titer did not drop for approximately 1 month. Addition of cyclodextrins to the formulation extended shelf life to 360 (beta cyclodextrin) and 690 (tertiary amine beta cyclodextrin) days which is significantly longer than that of virus in glycerol at –80° C. (~37 days, unreported observation).

TABLE 6

Expiration Dates for Adenoviral Formulations Stored at 4° C.

| Formulation | Expiration Date* |
| --- | --- |
| 0.4% Sucrose/0.4% Mannitol/0.001% Span 20 | 35 days |
| 1M Sucrose/KPBS/BCD | 20 days |
| 1M Sucrose/KPBS | 10 days |
| 1M Sucrose/DPBS | 8 days |
| 0.5M Sucrose/KPBS | 7 days |
| 0.25M Sucrose/KPBS | 2 days |
| DPBS | 15 minutes |

*Note: Expiration dates represent the time for a preparation to lose 10% (0.1 log) of the original titer.

All formulations stored at 4° C. significantly enhanced viral stability (Table 2). Sucrose formulations containing beta cyclodextrin and surfactant did not display significant drops in titer for approximately one month.

EXAMPLE 17

Stability of AAV Formulations

Initial stability studies with adeno-associated virus demonstrated that this virus is significantly more stable than the adenovirus.

TABLE 7

Expiration Dates for Adeno-Associated Virus Formulations.

| Formulation | −80° C. | −20° C. | 4° C. | 25° C. |
|---|---|---|---|---|
| 0.4% Sucrose 0.4% Mannitol 0.01% Pluronic Protamine (0.5 mg/ml) | 26.7 days | 89.5 days | 240 days | 24.7 days |
| 0.4% Sucrose 0.4% Mannitol 0.001% Span 20 Protamine (1.0 mg/ml) | 149.4 days | 149.65 days | 150.1 days | 153.5 days |
| DPBS 10% glycerol | 32.4 days | 37.4 days | n/d | n/d |
| DPBS | 27 days | n/d | 135.4 days | 125.5 days |

*Note: Expiration dates represent the time for the preparation to lose 10% (0.1 log) of the original titer.
n/d- stability not assessed at this temperature.

It took approximately 4 months for a preparation stored at 4° C. in sodium phosphate buffered saline to lose 0.1 log of infectious virus (Table 7). Similar results were seen at 25° C. A formulation consisting of sucrose, mannitol, Span 20 and protamine extended AAV stability to 5 months at 4 and 25° C. Similar expiration dates were also noted with this formulation at −20 and −80° C.

EXAMPLE 18

Effect of Formulation on Transduction Efficiency In Vivo

Because adenoviral vectors are suitable for many gene therapy applications, we studied the effect of these formulations on transduction efficiency after intramuscular, intravenous and intratracheal injection in C57BL/6 mice. Transduction efficiency of formulated virus was compared to vector in phosphate buffered saline and the standard 2% glycerol preparation commonly used in pre-clinical testing of viral vectors [F. Borellini and J. M. Ostrove, "The Transfer of Technology from the Laboratory to the Clinic: In Process Controls and Final Product Testing", in *Gene Therapy Technologies, Applications and Regulations*, A. Meager, Editor. 1999, John Wiley & Sons: West Sussex, England. p. 359–373]. A 5% glycerol formulation was also included as a semi-toxic control by which to compare our formulations.

A. In Vivo Testing of Formulated Virus

C57BL/6 mice (6–8 weeks old) were purchased from Jackson Laboratories (Bar Harbor, Me.). Preparations were administered either via the tail vein ($1 \times 10^{11}$ particles in 100 μl formulation), intratrachially ($5 \times 10^{10}$ particles in 50 μl), or intramuscularly ($5 \times 10^{10}$ particles in 50 μl). Four animals from each group were necropsied either 4 days (intravenous and intratracheal) or 7 days (intramuscular) after injection. Tissues were homogenized in 1 ml of lysis buffer using a Brinkman polytron. Extracts were centrifuged at 14,000 rpm for 10 minutes. Protein concentration of supernatants was determined with Bio-Rad DC Protein assay reagents and bovine serum albumin as a standard. Extracts were quick-frozen in dry ice and stored at −80° C. until assayed. β-gal concentrations were determined with a β-gal ELISA kit (Boehringer-Mannheim) according to manufacturer's instructions. Blood samples were collected from remaining animals of each group via the retro orbital sinus 4 and 7 days after injection for assessment of liver function by an outside contract lab (Antech, New York, N.Y.). All animals were bled prior to initiation of the study for assessment of baseline LFT.

B. Results

A significant increase in transgene expression was detected after intramuscular injection of the sucrose/beta cyclodextrin and 5% glycerol formulations. The other formulations did not effect gene expression in muscle and were well tolerated. While the sucrose/tertiary amine beta cyclodextrin formulation enhanced transduction efficiency of the virus in the lung, transduction efficiency was reduced by the 5% glycerol preparation. Signs of acute inflammation were detected in lungs from mice given this preparation (data not shown). This effect was not detected in animals given the other formulations. All formulations tested slightly enhanced transduction efficiency when administered intravenously. The 5% glycerol preparation produced a marked increase in SGOT/SGTP levels beyond that routinely observed after administration of vector. This was not seen with the other formulations.

EXAMPLE 19

Development of Lyophilized Viral Vectors

Even though the formulation efforts described herein significantly enhanced adenoviral stability at −20 and 4° C., they would still require shipment on ice. Lyophilization, a technique commonly employed to extend the chemical and physical stability of labile compounds at ambient temperatures, was considered as a practical alternative. The lyophilization process consists of three stages: freezing, primary drying and secondary drying. During the freezing step, samples are frozen in the range of −40 to −50° C. When the product is completely frozen, the pressure in the lyophilization chamber is reduced and heat is applied to the product. Under these conditions, water is removed by the sublimation, a phase change from the solid state directly to the vapor state without the appearance of an intermediate liquid phase. As freeze-drying proceeds, the thickness of the frozen layer decreases. This is the primary drying phase. After primary drying, additional drying is necessary to remove any water that remains in the product. During secondary drying, heat is slowly added to the highest allowable temperature to maintain product viability and maintained at this level until the process is complete.

A large batch of adenovirus was purified and divided into five separate groups. Each group was desalted into different formulations. Excipients were selected according to their ability replace water and form a protective shell around the viral capsid in order to maintain protein conformation during the freezing and drying process as described by Timasheff, Carpenter and others [Carpenter, J. F. and J. H. Crowe, *Cryobiology*, 25: 244–255 (1988); Crowe, J. H., et al., *Cryobiology*, 27: 219–231 (1990); Carpenter, J. F. and J. H. Crowe, *Biochemistry*, 28: 3916–3922 (1989); Timasheff, S. N., *Annu Rev Biophys Biomol Struct.*, 22: 67–97 (1993)]. The initial titer of the lot was $1 \times 10^{11}$ lfu/ml. One milliliter aliquots were placed in glass vials and lyophilized under a standard protocol (−40° C. for 2 hours, −33° C. for 12 hours, −25° C. for 5 hours, 10° C. for 4 hours and 20° C. for 8 hours at a pressure of 30 mtorr).

For each lyophilization study, a lot of virus was divided into two groups with one half desalted in the desired formulation and the other desalted in KPBS containing 10% glycerol. The latter preparation was stored at −20° C. and served as a control by which to assess the ability of lyophilization to enhance viral stability. Viral titers were assessed prior to storage at −20° C. and lyophilization (t=0). Vials containing the formulated preparation were placed in a single shelf research grade lyophilizer (FTS Systems, Stone Ridge, N.Y.) and cooled at a rate of 1° C./min to −40° C. Three vials of formulation without virus were fitted with lead platinum RTD temperature probes (FTS) and placed in the front, middle and back of the lyophilization unit to monitor product temperature changes during the process. After cooling, all samples were lyophilized according to methods tailored to the specific formulation under study [M. J. Pikal, Freeze-Drying of Proteins, Part 1: *Process Design. Biopharm.*, 1990, September: p. 18–27]. After drying was complete. samples were stoppered under vacuum and sealed with 13 mnm tear-off aluminum seals (Wheaton). Samples were stored at 4° C. until assayed for viral titer. Lyophilized virus was reconstituted with 1 ml sterile water for injection (USP) and assayed with samples stored at −20° C. in KPBS and 10% glycerol.

Figure 2:
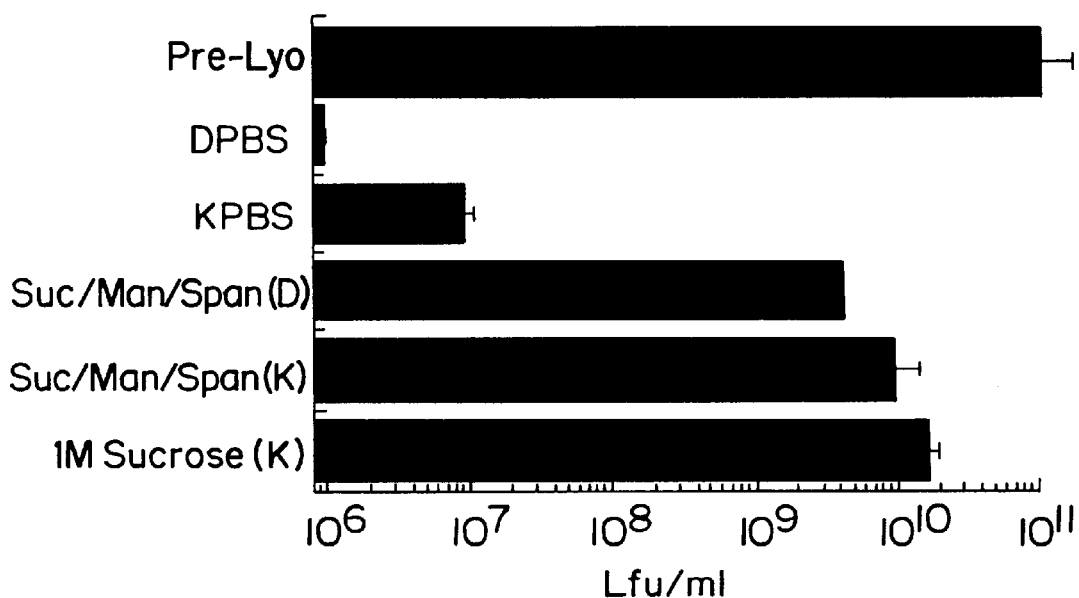
FIG. 2 illustrates the results of a study of the effect of the addition of excipients on adenoviral preparation on the recovery of active vector after lyophilization. Pre-lyophilization (Pre-lyo) titer for the entire lot was $1 \times 10^{11}$ lfu/ml. Concentrations of sucrose, mannitol and Span 20 in the Suc/Man/Span formulations are 40 mg/mL, 40 mg/mL and 0.001%, respectively. K=KPBS, D=DPBS. Data are the average of eight vials from two separate experiments. Error bars represent the standard error of the data.

Preparations lyophilized in sodium or potassium phosphate buffer alone suffered significant losses of 5 and 4 logs of infectious virus respectively (FIG. 2). When sucrose, mannitol and Span 20 were added to formulations, titer fell by approximately 1 log. Titer fell by less than 1 log in preparations lyophilized in 1M sucrose.

EXAMPLE 20

Effect of Viral Concentration on Glass Transition Temperature (Tg') of Formulations for Lyophilization Even though all excipients significantly improved recovery of adenovirus after lyophilization, each preparation still suffered a drop in titer, which was attributed to the process itself. Thus, formulations were further characterized in order to maximize viral recovery upon completion of the lyophilization cycle. One parameter that is important for ascertaining the required processing conditions is the glass transition temperature (Tg'), the temperature of maximum freeze concentration where, in a frozen solution, the residual non-ice phase forms a glass [F. Franks, *Cryo-Letters*, 11:93–100 (1990)]. If primary drying is carried out above Tg', the freeze concentrate behaves as a viscous liquid, the microstructure of ice formed upon freezing will be lost and product recovery is significantly hampered. If drying occurs below the Tg', water will be rapidly removed without disrupting the microstructure established upon freezing which minimizes product loss during lyophilizaton [F. Franks, *Develop. Biol. Stand.*, 74:9–19 (1991)]. Thus, the Tg' of a preparation sets the safe upper temperature limit for primary drying. Because Tg' can vary over an enormous range (−1 to −50° C.), determination of this value for a proposed formulation is extremely important and the first step in process development.

The Tg' of a preparation is very concentration dependent: buffer salts, amino acids, carbohydrates and other components added to a formulation can influence Tg' [te Booy, M. P. W. M., et al, *Pharmaceutical Res.*, 9(1):109–114 (1992)]. Differential scanning calorimetry (DSC) gives a direct measurement of Tg' [Her, L. M., et al., *Pharmaceutical Research*, 11(1): 54–59 (1994); Hatley, R. H. M., *Developments in Biological Standardization*, 74: 105–122 (1990); Hatley, R. H. M. a. F., F., *Journal of Thermal Analysis*, 37: 1905–1914 (1991)].

DSC analysis was performed with a MDSC 2920 (TA Instruments, New Castle, Del.) equipped with liquid nitrogen cooling. The calorimeter was calibrated for temperature and cell constant using indium. Fifty microliters of each formulation were analyzed in hermetically sealed aluminum pans (TA Instruments). The cooling rate was 1° C./min. The temperature range was −60 to +25° C. Glass transition values (Tg') are reported as the midpoint of the observed transition. Experiments were performed in duplicate.

Sucrose (1M) in potassium phosphate buffered saline has a glass transition of −34.5° C. (see Table 8 below).

TABLE 8

| Formulation | Particles/ml | Tg' (° C.) |
|---|---|---|
| 1 M Sucrose | 0 | −34.5 |
| 1 M Sucrose | $1 \times 10^{11}$ Ad | −33.9 |
| 1 M Sucrose | $1 \times 10^{12}$ Ad | −32.0 |
| 0.5 M Sucrose | 0 | −33.5 |
| 0.5 M Sucrose | $1.55 \times 10^{11}$ AAV | −34.71 |
| 0.5 M Sucrose | $1.53 \times 10^{12}$ AAV | −35.37 |

When adenovirus was added at a concentration of $1 \times 10^{11}$ particles/ml, the Tg' rose to −33.9° C. Addition of another log of virus pushed the glass transition temperature to −32.0° C. This effect is commonly seen with proteins [M. J. Pikal, *Biopharm*, September: 18–27 (1990); M. J. Pikal, *Pharmaceutical Res.*, 8(4):427–437 (1991)]. As protein replaces the water in a preparation, the glass transition rises. Adeno-associated virus had a different effect on the Tg' of a 0.5M sucrose formulation. Addition of the virus at a concentration of $1.55 \times 10^{11}$ genome copies/ml lowered the glass transition temperature from −33.5 to −34.71° C. Addition of another log of virus dropped Tg' to −35.37° C. These results suggest that this virus may interact with excipients in the frozen state differently than traditional proteins. Based on this information, the primary drying temperature for the Ad preparation was set at −35° C. AAV was dried at −38° C.

EXAMPLE 21

Effect of Final Moisture Content of the Lyophilized Cake on the Recovery of Adenovirus Various blends of sucrose and mannitol were tested for final moisture content after a standard lyophilization cycle (−40° C. for 2 hours, −35° C. for 11 hours, −10° C. for 2 hours, 0° C. for 2 hours and 25° C. for 3 hours at a pressure of 30 mtorr).

Water content of lyophilized formulations was determined by Karl Fischer titration [J. C. May, et al., *Dev. Biol. Stand*, 74:153–164 (1992)] and confirmed by thermogravimetric analysis (TGA) [J. C. May, et al., *J. Biol. Standardization*, 10:249–259 (1982)]. For Karl Fisher titration, an Aqua Star Karl Fischer titrator (Model C3000, EM Sciences) equipped with a fritless cell was calibrated with Karl Fischer water standard (2-methoxy ethanol) and blanked with the addition of 1 ml anhydrous methanol (EM Sciences). Lyophilized samples were reconstituted with anhydrous methanol and added to the titrator. TGA was performed with a Perkin-Elmer TGA 7 Series thermogravimetric system. Three to five milligrams of lyophilized preparation was scanned at 10° C./min from 25 to 200° C.

The data provided in Table 9 below are the average of 10 vials from a single lyophilization run.

TABLE 9

Final Moisture Content of the Lyophilized Cake Significantly Affects Recovery of Adenovirus.

| Sucrose:Mannitol Ratio | Pre-Lyo Titer (lfu/ml) | Post-Lyo Titer (lfu/ml) | Moisture Content |
|---|---|---|---|
| 1:4 | $5.12 \pm 0.01 \times 10^{11}$ | $4.6 \pm 0.2 \times 10^{10}$ | $0.6 \pm 0.01\%$ |
| 1:2 | $5.12 \pm 0.01 \times 10^{11}$ | $2.8 \pm 0.11 \times 10^{11}$ | $0.9 \pm 0.001\%$ |
| 3:4 | $5.12 \pm 0.01 \times 10^{11}$ | $4.77 \pm 0.04 \times 10^{11}$ | $1.3 \pm 0.07\%$ |
| 1:1 | $5.12 \pm 0.01 \times 10^{11}$ | $5.08 \pm 0.1 \times 10^{11}$ | $1.4 \pm 0.25\%$ |
| 2:1 | $5.12 \pm 0.01 \times 10^{11}$ | $2.89 \pm 0.3 \times 10^{11}$ | $1.6 \pm 0.1\%$ |
| 4:1 | $5.12 \pm 0.01 \times 10^{11}$ | $1.0 \pm 0.22 \times 10^{11}$ | $3.35 \pm 0.05\%$ |

When adenovirus was added to these preparations at a concentration of $5.12 \times 10^{11}$ lfu/ml, recovery of infectious virus was extremely sensitive to the final moisture content of the product (Table 9). A preparation of 1:4 sucrose:mannitol had a final moisture content of 0.6% and suffered a 1.1 log loss in viral titer. The 3:4 ratio, with a moisture content of 1.3%, lost less than 1 log of infectious virus. A preparation consisting of a 1:1 ratio of sucrose:mannitol did not experience any loss of titer during the entire lyophilization process. The moisture content of this preparation was 1.4%. If water content rose 0.2% beyond this to 1.6%, titer fell by 2.2 log units. These data indicate that adenovirus is not only sensitive to the final water content in the lyophilized product, but that there is a rather narrow window in which viral titer can be maintained. As a result, all adenoviral lyophilization processes were tailored to produce a final moisture content of 1.3–1.5% in order to afford maximum recovery of virus.

EXAMPLE 22

Effect of Virus Concentration on Recovery of Viral Titer after Lyphilization

In order to assess the maximum allowable concentration of adenovirus that facilitates optimal recovery of viral titer after lyophilization, adenovirus was lyophilized at two different concentrations in two separate formulations. The results provided in Table 10 are the averages of 10 vials of each preparation.

TABLE 10

Effect of Initial Adenoviral Concentration on the Recovery of Infectious Virus after Lyophilization.

| Formulation Sucrose:Mannitol Ratio | Pre-Lyo Titer (lfu/ml) | Post-Lyo Titer (lfu/ml) |
|---|---|---|
| 1:4 | $5.2 \pm 0.04 \times 10^{10}$ | $4.6 \pm 0.01 \times 10^{9}$ |
| 1:4 | $5.5 \pm 0.1 \times 10^{11}$ | $2.97 \pm 0.1 \times 10^{11}$ |
| 4:1 | $1.9 \pm 0.2 \times 10^{10}$ | $1.0 \pm 0.02 \times 10^{9}$ |
| 4:1 | $2.0 \pm 0.14 \times 10^{11}$ | $1.6 \pm 0.1 \times 10^{11}$ |

In general, preparations with higher initial titers produced better recovery of active virus after lyophilization. Preparations at low viral concentration ($2-5 \times 10^{10}$ lfu/ml) suffered a loss of approximately one log of virus regardless of formulation. The loss in titer was less than one log at higher adenovirus concentrations ($2-5 \times 10^{11}$ lfu/ml). This is believed to be in part due to the ability of the virus itself to assist in maintaining the final frozen pH of a preparation upon freezing at high concentrations (data not shown). Adenovirus preparations of $1-5 \times 10^{11}$ lfu/ml were used in additional lyophilization studies.

EXAMPLE 23

Stability of Lyophilized Viral Vectors

After careful evaluation of process and formulation effects, a large-scale preparation of adenovirus ($1 \times 10^{11}$ lfu/ml) was lyophilized in a 1M sucrose formulation under the following protocol: $-40°$ C. for 2 hours, $-35°$ C. for 9 hours, $-10°$ C. for 4 hours, $0°$ C. for 4 hours and $25°$ C. for 8 hours at a pressure of 30 mtorr. After lyophilization, some vials were reconstituted.

The only loss detected in this preparation after one year at $4°$ C. was the initial loss of 0.5 log of virus due to the process itself. Virus from the same lot prepared in 10% glycerol and stored at $-20°$ C. suffered a drop in titer of approximately 2 logs over the same time period. The stability of reconstituted preparations stored at $4°$ C. was also assessed. Virus titer dropped at a steady rate of 0.5 log/day over a period of 4 days, indicating that the vector must be used soon after reconstitution. This degradation rate was similar for other lyophilized preparations regardless of formulation (data not shown). Studies to elucidate the nature of this rapid decline in titer and develop novel admixtures for reconstitution which promote viral stability are currently underway.

Little work was done with respect to the development of formulations and optimization of the lyophilization process for AAV vectors. In a single experiment, half of an AAV preparation ($8.7 \times 10^{8}$ lfu/ml) was desalted into potassium phosphate buffered saline. The remaining half was desalted in a formulation of 0.4% sucrose, 0.4% mannitol and protamine. Each preparation was lyophilized under the following protocol: $-40°$ C. for 2 hours, $-38°$ C. for 11 hours, $-10°$ C. for 2 hours, $0°$ C. for 2 hours, and $25°$ C. for 3 hours at a pressure of 30 mtorr.

After an initial loss of 0.3 log in titer due to the lyophilization process, the formulated preparation did not experience any loss in infectivity for 90 days at $25°$ C. It is also important to note that the preparation prepared in buffer without any additional excipients (Buffer) experienced a similar loss in titer after lyophilization. This suggests that AAV may be resistant to the stresses of the freeze-drying process.

All publications cited in this specification are incorporated herein by reference herein. While the invention has been described with reference to a particularly preferred embodiment, it will be appreciated that modifications can be made without departing from the spirit of the invention. Such modifications are intended to fall within the scope of the appended claims.

What is claimed is:

1. A method for conjugating a recombinant virus with polyethylene glycol to enhance transduction efficiency thereof, said method comprising the steps of:
    a) reacting activated polyethylene glycol and a recombinant virus at ambient temperature for about 1 to about 2 hours at a ratio of about 10:1 polyethylene glycol to virus; and
    b) stopping the reaction, thereby obtaining polyethylene glycol conjugated virus.
2. The method according to claim 1, wherein the reaction takes place in solution and the recombinant virus is present at a concentration of about $1 \times 10^{10}$ to about $1 \times 10^{15}$ particles per ml of solution.
3. The method according to claim 1, wherein the polyethylene glycol is activated with a compound selected from the group consisting of tresyl chloride, succinimidyl succinate and cyanuric chloride.

4. The method according to claim 1, wherein the polyethylene glycol has a molecular weight of 5000 daltons.

5. The method according to claim 1, wherein the polyethylene glycol is a monomethyoxypolyethylene glycol.

6. The method according to claim 1, wherein said recombinant virus is an adenovirus.

7. A polyethylene-glycol conjugated recombinant virus, said virus prepared according to the method of claim 1.

8. A composition useful for delivery of a selected molecule to host cells, said composition comprising a polyethylene-glycol conjugated recombinant virus prepared according to the method of claim 1 and a physiologically acceptable carrier.

9. A method for conjugating a recombinant adeno-associated virus with polyethylene glycol to enhance transduction efficiency thereof, said method comprising the steps of:
   a) reacting activated polyethylene glycol and a recombinant adeno-associated virus at ambient temperature for about 1 to about 2 hours; and
   b) stopping the reaction, thereby obtaining polyethylene glycol conjugated adeno-associated virus.

10. The method according to claim 9, wherein the reaction takes place in solution and the recombinant adeno-associated virus is present at a concentration of about $1 \times 10^{10}$ to about $1 \times 10^{15}$ particles per ml of solution.

11. The method according to claim 9, wherein the polyethylene glycol is activated with a compound selected from the group consisting of tresyl chloride, succinimidyl succinate and cyanuric chloride.

12. The method according to claim 9, wherein the polyethylene glycol has a molecular weight of 5000 daltons.

13. The method according to claim 9, wherein the polyethylene glycol is a monomethyoxypolyethylene glycol.

14. A polyethylene-glycol conjugated recombinant adeno-associated virus, said virus prepared according to the method of claim 9.

15. A composition useful for delivery of a selected molecule to host cells, said composition comprising a polyethylene-glycol conjugated recombinant adeno-associated virus prepared according to the method of claim 9 and a physiologically acceptable carrier.

16. The virus according to claim 7, wherein said virus is selected from the group consisting of an adenovirus and an adeno-associated virus.

17. The virus according to claim 7, wherein said virus is conjugated with monomethyoxypolyethylene glycol.

18. A method for re-administration of a molecule to a selected host cell via a viral vector, said method comprising the steps of:
   (a) contacting the host cell with a polyethyleneglycol (PEG)-modified recombinant virus according to claim 7, wherein said virus comprises a molecule for delivery to a host cell; and
   (b) contacting the host cells with a recombinant virus comprising the molecule.

19. A method for increasing transduction efficiency of a recombinant virus, said method comprising the steps of:
   (a) conjugating a recombinant virus with polyethyleneglycol by
      (i) reacting activated polyethylene glycol and a recombinant virus at ambient temperature for about 1 to about 2 hours at a ratio of about 10:1 polyethylene glycol to virus; and
      (ii) stopping the reaction, thereby obtaining polyethylene glycol conjugated virus with increased transduction efficiency; and
   (b) delivering the polyethylene-glycol conjugated virus to host cells.

20. The method according to claim 18, wherein the host cells are contacted with the PEG-modified recombinant virus subsequent to contacting the host cells with a recombinant virus comprising the molecule.

21. The method according to claim 18, wherein the recombinant virus comprising the molecule is a second PEG-modified virus.

22. The method according to claim 21, wherein in the first PEG-modified recombinant virus and the second PEG-modified virus, the PEG is monomethoxy PEG (MPEG) and for each virus, the MPEG has been activated by different groups.

23. The method according to claim 22, wherein the MPEG is activated with a compound selected from the group consisting of tresyl chloride, succinimidyl succinate and cyanuric chloride.

24. A composition that enhances the physical stability of viral vectors, said composition comprising:
   (a) a recombinant viral vector comprising a molecule for delivery to host cells;
   (b) sucrose; and
   (c) mannitol, wherein the ratio of sucrose to mannitol is about 1 to about 1.

25. The composition according to claim 24, wherein the composition is lyophilized to a final moisture content of about 1.2% to about 1.7%.

26. The composition according to claim 24, wherein the composition in solution comprises about $1 \times 10^{10}$ to about $1 \times 10^{15}$ particles recombinant virus per milliliter solution.

27. The composition according to claim 24, further comprising a beta cyclodextrin.

28. The composition according to claim 24, further comprising a protamine.

29. A method for re-administration of a molecule to a selected host cell via a viral vector, said method comprising the steps of:
   (a) contacting the host cell with a polyethylene glycol (PEG)-modified recombinant adeno-associated virus according to claim 14, wherein said virus comprises a molecule for delivery to a host cell; and
   (b) contacting the host cells with a recombinant virus comprising the molecule.

30. A method for increasing transduction efficiency of a recombinant adeno-associated virus, said method comprising the steps of:
   (a) conjugating a recombinant adeno-associated virus with polyethylene-glycol by
      i) reacting activated polyethylene glycol and a recombinant adeno-associated virus at ambient temperature for about 1 to about 2 hours; and
      ii) stopping the reaction, thereby obtaining polyethylene glycol conjugated adeno-associated virus; and
   (b) delivering the polyethylene-glycol conjugated virus to host cells.

31. The method according to claim 29, wherein the host cells are contacted with the PEG-modified recombinant adeno-associated virus subsequent to contacting the host cells with a recombinant virus comprising the molecule.

32. The method according to claim 29, wherein in the first PEG-modified recombinant adeno-associated virus and the second PEG-modified virus, the PEG is monomethoxy PEG (MPEG) and for each virus, the MPEG has been activated by different groups.

33. The method according to claim 31, wherein the recombinant virus comprising the molecule is a second PEG-modified virus.

34. The method according to claim 32, wherein the MPEG is activated with a compound selected from the group consisting of tresyl chloride, succinimidyl succinate and cyanuric chloride.

* * * * *